(12) United States Patent
Amino et al.

(10) Patent No.: US 10,144,717 B2
(45) Date of Patent: *Dec. 4, 2018

(54) CYSTEINE DERIVATIVE

(71) Applicant: AJINOMOTO CO., INC., Tokyo (JP)

(72) Inventors: Yusuke Amino, Kawasaki (JP); Yoshinobu Takino, Kawasaki (JP); Shinji Kuroda, Kawasaki (JP); Keiji Iwasaki, Kawasaki (JP); Megumi Kaneko, Kawasaki (JP); Fumie Okura, Kawasaki (JP)

(73) Assignee: AJINOMOTO CO., INC., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/934,596

(22) Filed: Nov. 6, 2015

(65) Prior Publication Data

US 2016/0060234 A1 Mar. 3, 2016

Related U.S. Application Data

(60) Division of application No. 13/686,384, filed on Nov. 27, 2012, now Pat. No. 9,212,154, which is a continuation of application No. PCT/JP2011/062293, filed on May 27, 2011.

(30) Foreign Application Priority Data

May 28, 2010 (JP) ................. 2010-123169

(51) Int. Cl.
| | |
|---|---|
| C07D 277/06 | (2006.01) |
| A61K 8/49 | (2006.01) |
| A61Q 19/02 | (2006.01) |
| A61Q 1/02 | (2006.01) |
| A61Q 15/00 | (2006.01) |
| A61Q 17/00 | (2006.01) |
| C07D 417/04 | (2006.01) |
| C07D 513/08 | (2006.01) |
| C07K 5/06 | (2006.01) |
| C07K 5/078 | (2006.01) |

(52) U.S. Cl.
CPC .............. *C07D 277/06* (2013.01); *A61K 8/49* (2013.01); *A61K 8/4926* (2013.01); *A61Q 1/02* (2013.01); *A61Q 15/00* (2013.01); *A61Q 17/00* (2013.01); *A61Q 19/02* (2013.01); *C07D 417/04* (2013.01); *C07D 513/08* (2013.01); *C07K 5/06139* (2013.01)

(58) Field of Classification Search
CPC ...... A61K 8/49; A61K 8/4926; A61K 31/426; A61K 8/361; A61K 8/368; A61K 8/44; A61K 8/445; A61K 8/4973; A61K 8/498; A61K 8/602; A61K 8/64; A61K 8/97; A61Q 19/02; A61Q 1/02; A61Q 15/00; A61Q 17/00; A61Q 19/00; A61Q 5/02; A61Q 5/12; C07K 5/06139

See application file for complete search history.

(56) References Cited

U.S. PATENT DOCUMENTS

| | | |
|---|---|---|
| 6,229,041 B1 | 5/2001 | Brown et al. |
| 6,602,492 B2 | 8/2003 | Iwasaki et al. |
| 2003/0095959 A1 | 5/2003 | Mayne |
| 2004/0006115 A1 | 1/2004 | Galey et al. |
| 2007/0232574 A1 | 10/2007 | Galey et al. |
| 2009/0163545 A1 | 6/2009 | Goldfarb |
| 2010/0179200 A1 | 7/2010 | Galey et al. |

FOREIGN PATENT DOCUMENTS

| | | |
|---|---|---|
| DE | 27 29 414 A1 | 1/1978 |
| GB | 811816 | 4/1959 |
| JP | 48-15938 | 5/1973 |
| JP | 2004-517063 | 6/2004 |
| JP | 2009-227660 | 10/2009 |
| JP | 2010-001239 | 1/2010 |

OTHER PUBLICATIONS

Cremonesi et al (Tetrahedron: Asymmetry, 2005, vol. 16, pp. 3371-3379).*
Sheehan et al. (Journal of the American Chemical Society, 1952, vol. 74, pp. 4957-4958).*
Refouvelet et al. (Journal of Heterocyclic Chem, 1994, vol. 31, pp. 77-80).*
Schubert—"Reactions of Semimercaptals with amino compounds", 1937, Journal of Biological Chemistry, vol. 121, pp. 539-548.
Office Action dated Apr. 9, 2013, in Japanese Patent Application No. 2012-517348 (with English Translation).
Cremonesi G. et al., "Asymmetric synthesis of 1,3-thiazolidine-derived spiro-β-lactams via a Staudinger reaction between chiral ketenes and imines", Tetrahedron Asymmetry, vol. 16 (2005) pp. 3371-3379.

(Continued)

*Primary Examiner* — Mark V Stevens
(74) *Attorney, Agent, or Firm* — Oblon, McClelland, Maier & Neustadt, L.L.P.

(57) ABSTRACT

Cysteine compounds represented by the following formula

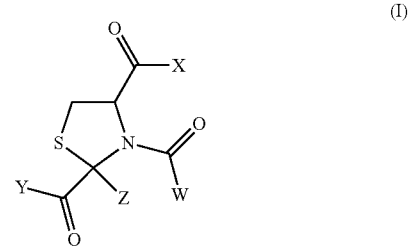

(I)

wherein each symbol is as defined in the specification, and salts thereof, are superior in stability, have less odor, exhibit an eumelanin production suppressive effect, and are useful as cosmetic agents.

9 Claims, 2 Drawing Sheets

(56) References Cited

OTHER PUBLICATIONS

Nallet J. P. et al., "Synthesis of a Series of Hexitol and Aminodeoxyhexitol Mononitrate Derivatives Containing a Sulfur Group and Pharmacological Evaluation on Isolated Rat Aortas", J. Org. Chem., (1998) pp. 933-943.

International Search Report issued in PCT/JP2011/062293 dated Sep. 6, 2011.

X. Fernandez et al., "Thiazolidines and their oxidation products as flavouring compunds", Flavour and Fragrance Journal, vol. 17, (2002) pp. 432-439.

T. Akasaka et al., "Cooxidation Reaction in the Singlet Oxygenation of Cyclic and Benzylic Sulfides: S-Hydroperoxysulfonium Ylide Intermediate as a New Epoxidizing Species", J. Am. Chem. Soc., vol. 113 (1991) pp. 2696-2701.

H. Jamet et al., "NMR and Theoretical Calculations: A unified view of the Cis/Trans Isomerization of 2-Substituted Thiazolidines Containing Peptides" J. Phys. Chem. B, vol. 112, (2008) pp. 9975-9981.

Extended European Search Report dated Jun. 25, 2013 in Patent Application No. 11786790.3.

Giuseppe Cremonesi, et al., "Stereoselective synthesis of 4-substituted azetidine-2, 3-diones by ring opening of 1, 3-thiazolidine-derived spiro-β-lactams", Tetrahedron: Asymmetry, XP 22520486A, vol. 19, No. 5, Mar. 7, 2008, pp. 554-561.

Hitoshi Nagaoka, et al., 2-(3-Pyridyl) thiazolidine-4-carboxamides. 1. Novel Orally Active Antagonists of Platelet-Activating Factor (PAF), Chem. Pharm. Bull., XP002698114A, vol. 45, No. 10, 1997, pp. 1659-1664.

Li Hong, et al., "Application of chiral thiazolidine ligands to asymmetric hydrosilation", Science in China (Series B), XP002698115A, vol. 40, No. 5, Oct. 1997, pp. 485-490.

Z. Györgydeák, et al., "Heterocyclische Verbindungen aus Zuckern, XV [1]: Zur Konfiguration chiraler C-2-substituierter 4-Thiazolidincarbonsäuren. Chiralitätstransfer auf C-3 in 3, 4-Dihydro-1H-pyrrolo [1,2-c] thiazolen", Monatshefte für Chemie, XP002518651A, vol. 125, 1994, pp. 189-208.

Ando et al. "Acylation of 2,4-Disubstituted Thiazolidines and Oxazolidines", Chemistry Letters (1987), pp. 1361-1364.

* cited by examiner

CYSTEINE DERIVATIVE

CROSS REFERENCES TO RELATED APPLICATIONS

This application is a divisional of U.S. patent application Ser. No. 13/686,384, filed on Nov. 27, 2012, which is a continuation of International Patent Application No. PCT/JP2011/062293, filed on May 27, 2011, and claims priority to Japanese Patent Application No. 2010-123169, filed on May 28, 2010, each of which are incorporated herein by reference in their entireties.

BACKGROUND OF THE INVENTION

Field of the Invention

The present invention relates to particular cysteine derivatives. Furthermore, the present invention relates to methods for producing particular cysteine derivatives, cosmetic agents which contain particular cysteine derivatives, and the like.

Discussion of the Background

In human pigment cells (melanocytes) in the skin, melanin is produced utilizing L-cysteine and L-tyrosine. When a greater amount of L-tyrosine, which is a starting material for eumelanin, is utilized for the synthesis of melanin, production of eumelanin is promoted and the skin becomes dark. On the other hand, when a greater amount of L-cysteine is utilized for the synthesis of melanin, production of eumelanin is suppressed, and the skin becomes closer to yellow. Therefore, it is considered that production of eumelanin is suppressed by supplying L-cysteine during melanin synthesis.

Heretofore, many attempts have been made to utilize L-cysteine as cosmetics such as whitening agents utilizing L-cysteine and the like. However, L-cysteine is easily oxidized, and has problems such as poor stability and bad odor for formulating as a cosmetic agent or skin external preparation.

To solve such problem, the development of a cysteine derivative with improved stability has been considered. JP-B-48-15938 discloses that L-2-methylthiazolidine-2,4-dicarboxylic acid is extremely stable as compared to conventional cysteine derivatives.

In addition, JP-A-2009-227660 discloses that a cysteine derivative obtained by esterification of L-2-methylthiazolidine-2,4-dicarboxylic acid or a salt thereof is useful as a whitening agent etc. since it has an eumelanin production suppressive effect and is stable. Furthermore, JP-A-2010-1239 discloses that 2-methylthiazolidine-2,4-dicarboxylic acid or a derivative thereof has a whitening action.

On the other hand, J. Biological Chem., (1937) 121 539-48 discloses N-acetyl-2-methylthiazolidine-2,4-dicarboxylic acid and N-acetyl-2-methylthiazolidine-2,4-dicarboxylic acid anhydride; however, it does not describe their properties such as stability etc. and physiological activities thereof, nor does it suggest or report use for cosmetic agents or skin external preparations or whitening effects thereof.

SUMMARY OF THE INVENTION

Accordingly, it is one object of the present invention to provide novel cysteine derivatives.

It is another object of the present invention to provide novel cysteine derivatives having an eumelanin production suppressive effect.

It is another object of the present invention to provide novel cysteine derivatives which exhibit superior stability.

It is another object of the present invention to provide novel cysteine derivatives which have less odor.

It is another object of the present invention to provide novel methods for producing such a cysteine derivative.

It is another object of the present invention to provide novel cosmetic agents which contain such a cysteine derivative.

It is another object of the present invention to provide novel cosmetic compositions which are superior in long-term preservation stability.

These and other objects, which will become apparent during the following detailed description, have been achieved by the inventors' discovery that particular cysteine derivatives are particularly superior in the stability, have less odor, and show a sufficient eumelanin production suppressive effect in a cell assay.

Accordingly, the present invention provides the following:

(1) A cosmetic agent, comprising a cysteine derivative represented by formula (I):

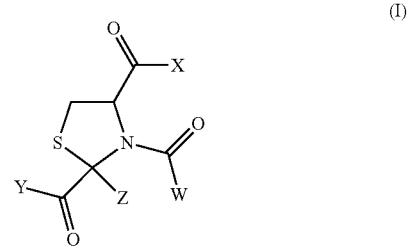

wherein
X and Y are each independently $OR^1$ or $NHR^2$ wherein $R^1$ and $R^2$ are each independently a hydrogen atom or a $C_{1-22}$ alkyl group, or an optionally modified amino acid residue, or X and Y in combination optionally form —O—;
Z is a hydrogen atom or a $C_{1-22}$ alkyl group; and
W is a $C_{1-22}$ alkyl group, a $C_{1-22}$ alkoxy group or a $C_{1-22}$ alkylamino group,
or a salt thereof.

(2) The cosmetic agent of the above-mentioned (1), wherein the cysteine derivative is one or more kinds selected from N-acetyl-2-methylthiazolidine-2,4-dicarboxylic acid, and N-acetyl-2-methylthiazolidine-2,4-dicarboxylic acid 2-ethyl ester, and a salt thereof.

(3) The cosmetic agent of the above-mentioned (1), wherein the cysteine derivative is one or more kinds selected from a trans form of N-acetyl-2-methylthiazolidine-2,4-dicarboxylic acid, and a trans form of N-acetyl-2-methylthiazolidine-2,4-dicarboxylic acid 2-ethyl ester, and a salt thereof.

(4) A cosmetic agent comprising a cysteine derivative represented by formula (IX):

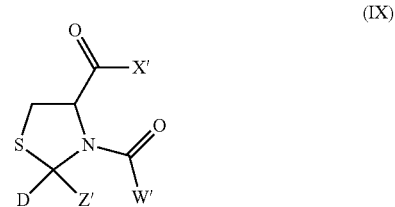

wherein
X' is $OR^1$ or $NHR^2$ wherein $R^1$ and $R^2$ are each independently a hydrogen atom or a $C_{1-22}$ alkyl group, or an optionally modified amino acid residue;

D is (1) an aromatic heterocyclic group optionally substituted by substituent(s) selected from
  (i) a hydroxyl group, and
  (ii) a $C_{1-6}$ alkyl group optionally substituted by hydroxyl group(s), or (2) a $C_{1-22}$ alkyl group optionally substituted by hydroxyl group(s);

Z' is a hydrogen atom or a $C_{1-22}$ alkyl group; and

W' is a $C_{1-22}$ alkyl group, a $C_{1-22}$ alkoxy group or a $C_{1-22}$ alkylamino group, or a salt thereof.

(5) A whitening agent comprising a cysteine derivative represented by formula (I):

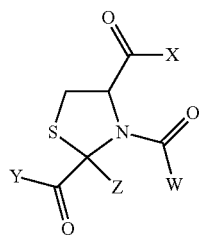

(I)

wherein

X and Y are each independently $OR^1$ or $NHR^2$ wherein $R^1$ and $R^2$ are each independently a hydrogen atom or a $C_{1-22}$ alkyl group, or an optionally modified amino acid residue, or X and Y in combination optionally form —O—;

Z is a hydrogen atom or a $C_{1-22}$ alkyl group; and

W is a $C_{1-22}$ alkyl group, a $C_{1-22}$ alkoxy group or a $C_{1-22}$ alkylamino group, or a salt thereof.

(5a) The whitening agent of the above-mentioned (5), wherein the cysteine derivative is one or more kinds selected from N-acetyl-2-methylthiazolidine-2,4-dicarboxylic acid, and N-acetyl-2-methylthiazolidine-2,4-dicarboxylic acid 2-ethyl ester, and a salt thereof.

(5b) The whitening agent of the above-mentioned (5), wherein the cysteine derivative is one or more kinds selected from a trans form of N-acetyl-2-methylthiazolidine-2,4-dicarboxylic acid, and a trans form of N-acetyl-2-methylthiazolidine-2,4-dicarboxylic acid 2-ethyl ester, and a salt thereof.

(5c) A whitening agent comprising a cysteine derivative represented by formula (IX):

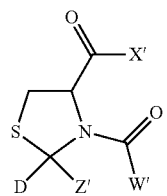

(IX)

wherein

X' is $OR^1$ or $NHR^2$ wherein $R^1$ and $R^2$ are each independently a hydrogen atom or a $C_{1-22}$ alkyl group, or an optionally modified amino acid residue;

D is (1) an aromatic heterocyclic group optionally substituted by substituent(s) selected from
  (i) a hydroxyl group, and
  (ii) a $C_{1-6}$ alkyl group optionally substituted by hydroxyl group(s), or (2) a $C_{1-22}$ alkyl group optionally substituted by hydroxyl group(s);

Z' is a hydrogen atom or a $C_{1-22}$ alkyl group; and

W' is a $C_{1-22}$ alkyl group, a $C_{1-22}$ alkoxy group or a $C_{1-22}$ alkylamino group, or a salt thereof.

(6) A cysteine derivative represented by formula (I):

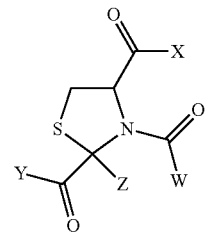

(I)

wherein

X and Y are each independently $OR^1$ or $NHR^2$ wherein $R^1$ and $R^2$ are each independently a hydrogen atom or a $C_{1-22}$ alkyl group, or an optionally modified amino acid residue, or X and Y in combination optionally form —O—;

Z is a hydrogen atom or a $C_{1-22}$ alkyl group; and

W is a $C_{1-22}$ alkyl group, a $C_{1-22}$ alkoxy group or a $C_{1-22}$ alkylamino group, provided that N-acetyl-2-methylthiazolidine-2,4-dicarboxylic acid, and N-acetyl-2-methylthiazolidine-2,4-dicarboxylic acid anhydride are excluded, or a salt thereof.

(6a) The cysteine derivative or salt of the above-mentioned (6), which is a trans form.

(7) A cysteine derivative represented by formula (IX):

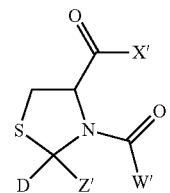

(IX)

wherein

X' is $OR^1$ or $NHR^2$ wherein $R^1$ and $R^2$ are each independently a hydrogen atom or a $C_{1-22}$ alkyl group, or an optionally modified amino acid residue;

D is (1) an aromatic heterocyclic group optionally substituted by substituent(s) selected from
  (i) a hydroxyl group, and
  (ii) a $C_{1-6}$ alkyl group optionally substituted by hydroxyl group(s), or (2) a $C_{1-22}$ alkyl group optionally substituted by hydroxyl group(s);

Z' is a hydrogen atom or a $C_{1-22}$ alkyl group; and

W' is a $C_{1-22}$ alkyl group, a $C_{1-22}$ alkoxy group or a $C_{1-22}$ alkylamino group, or a salt thereof.

(7a) The cysteine derivative or salt of the above-mentioned (7), which is a trans form.

(8) Trans N-acetyl-2-methylthiazolidine-2,4-dicarboxylic acid, or a salt thereof.

(9) Trans N-acetyl-2-methylthiazolidine-2,4-dicarboxylic acid 2-ethyl ester, or a salt thereof.

(10) Trans N-acetyl-2-methylthiazolidine-2,4-dicarboxylic acid 2-ethyl ester, or a salt thereof, of the above-mentioned (9), which is a crystal form.

(11) Trans N-acetyl-2-methylthiazolidine-2,4-dicarboxylic acid 2-ethyl ester, or a salt thereof, of the above-mentioned (10), which has melting point of 138° C. to 141° C.

(12) A method of producing a cysteine derivative represented by formula (I):

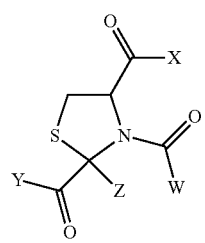

(I)

wherein

X and Y are each independently OR' or $NHR^2$ wherein $R^1$ and $R^2$ are each independently a hydrogen atom or a $C_{1-22}$ alkyl group, or an optionally modified amino acid residue, or X and Y in combination optionally form —O—;

Z is a hydrogen atom or a $C_{1-22}$ alkyl group; and

W is a $C_{1-22}$ alkyl group, a $C_{1-22}$ alkoxy group or a $C_{1-22}$ alkylamino group, provided that N-acetyl-2-methylthiazolidine-2,4-dicarboxylic acid, and N-acetyl-2-methylthiazolidine-2,4-dicarboxylic acid anhydride are excluded, which comprises reacting a compound represented by formula (IV):

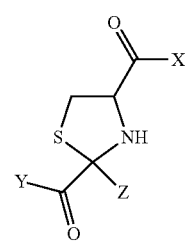

(IV)

wherein each symbol is as defined above, with a compound represented by formula (V):

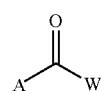

(V)

wherein

A is a halogen atom; and

W is as defined above, or a compound represented by formula (V'):

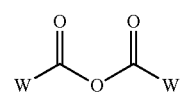

(V')

wherein W is as defined above.

(13) A method of selectively producing a trans form of a cysteine derivative represented by formula (I'):

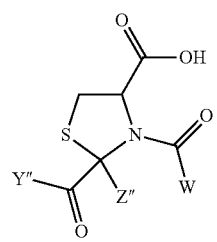

(I')

wherein

Y" is a $C_{1-22}$ alkoxy group;

Z" is a $C_{1-22}$ alkyl group; and

W is a $C_{1-22}$ alkyl group, a $C_{1-22}$ alkoxy group or a $C_{1-22}$ alkylamino group, or a salt thereof, which comprises reacting a compound represented by formula (IV'):

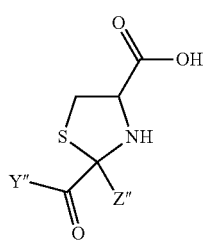

(IV')

wherein each symbol is as defined above, with a compound represented by formula (V):

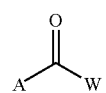

(V)

wherein
A is a halogen atom; and
W is as defined above,
in the presence of an organic base, or
with a compound represented by formula (V'):

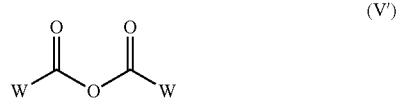

wherein W is as defined above,
in the absence of a base.

The present invention provides cysteine derivatives having superior stability, less odor and an eumelanin production suppressive effect, which enables provision of a whitening agent, cosmetic agent or skin external preparation, which contains the derivative as an active ingredient and is superior in the long-term preservation stability.

BRIEF DESCRIPTION OF THE DRAWINGS

A more complete appreciation of the present invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
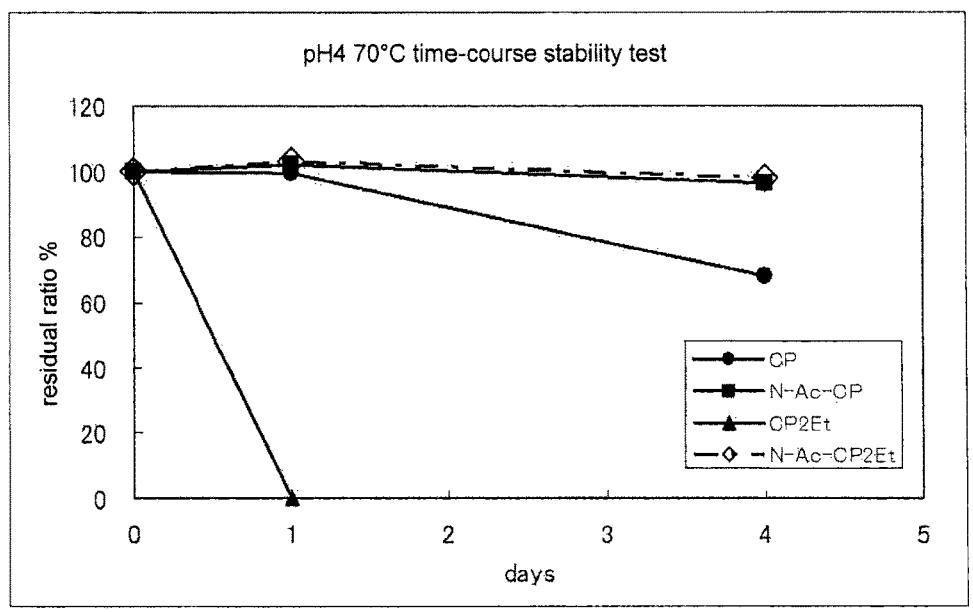
FIG. 1 shows the results of a time-course stability test of 2-methylthiazolidine-2,4-dicarboxylic acid (CP), N-acetyl-2-methylthiazolidine-2,4-dicarboxylic acid (N-Ac-CP), 2-methylthiazolidine-2,4-dicarboxylic acid 2-ethyl ester (CP2Et) and N-acetyl-2-methylthiazolidine-2,4-dicarboxylic acid 2-ethyl ester (N-Ac-CP2Et) at pH 4, 70° C.

The terms to be used in the present specification are defined in the following.

The term "$C_{1-22}$ alkyl group" means a straight chain or branched chain hydrocarbon group having 1 to 22 carbon atoms, and examples thereof include a methyl group, an ethyl group, an isopropyl group, a propyl group, a butyl group, an isobutyl group, a sec-butyl group, a tert-butyl group, a pentyl group, a sec-pentyl group, a tert-pentyl group, an isopentyl group, a hexyl group, a heptyl group, an octyl group, a 2-ethylhexyl group, a tert-octyl group, a nonyl group, an isononyl group, a decyl group, an isodecyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, an isooctadecyl group, an oleyl group, a behenyl group, and the like.

Examples of the "$C_{1-16}$ alkyl group" include a methyl group, an ethyl group, an isopropyl group, a propyl group, a butyl group, an isobutyl group, a sec-butyl group, a tert-butyl group, a pentyl group, a sec-pentyl group, a tert-pentyl group, an isopentyl group, a hexyl group, a heptyl group, an octyl group, a 2-ethylhexyl group, a tert-octyl group, a nonyl group, an isononyl group, a decyl group, an isodecyl group, an undecyl group, a dodecyl group, a tridecyl group, an isotridecyl group, a tetradecyl group, a pentadecyl group, a hexadecyl group, an isohexadecyl group, and the like.

Examples of the "$C_{1-6}$ alkyl group" include a methyl group, an ethyl group, an isopropyl group, a propyl group, a butyl group, an isobutyl group, a sec-butyl group, a tert-butyl group, a pentyl group, a sec-pentyl group, a tert-pentyl group, an isopentyl group, a hexyl group, and the like.

The term "$C_{1-22}$ alkoxy group" means a hydroxyl group substituted by the above-mentioned "$C_{1-22}$ alkyl group", and examples thereof include a methoxy group, an ethoxy group, a propoxy group, an isopropyloxy group, a butoxy group, an isobutyloxy group, a tert-butyloxy group, a pentyloxy group, a hexyloxy group, a heptyloxy group, an octyloxy group, a nonyloxy group, a decyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a nonadecyloxy group, an eicosyloxy group, a heneicosyloxy group, a docosyloxy group, and the like.

Examples of the "$C_{1-6}$ alkoxy group" include a methoxy group, an ethoxy group, a propoxy group, an isopropyloxy group, a butoxy group, an isobutyloxy group, a tert-butyloxy group, a pentyloxy group, a hexyloxy group, and the like.

The term "$C_{1-22}$ alkylamino group" means an amino group substituted by the above-mentioned "$C_{1-22}$ alkyl group(s)", and examples thereof include a methylamino group, an ethylamino group, a propylamino group, an isopropylamino group, a butylamino group, an isobutylamino group, a tert-butylamino group, a pentylamino group, a hexylamino group, a heptylamino group, an octylamino group, a nonylamino group, a decylamino group, an undecylamino group, a dodecylamino group, a tridecylamino group, a tetradecylamino group, a pentadecylamino group, a hexadecylamino group, a heptadecylamino group, an octadecylamino group, a nonadecylamino group, an eicosylamino group, a heneicosylamino group, a docosylamino group, and the like.

Examples of the "$C_{1-6}$ alkylamino group" include a methylamino group, an ethylamino group, a propylamino group, an isopropylamino group, a butylamino group, an isobutylamino group, a tert-butylamino group, a pentylamino group, and a hexylamino group.

Examples of "halogen atom" include a chlorine atom, a bromine atom, a fluorine atom, and an iodine atom.

Each substituent in the above-mentioned formula (I) is explained in the following.

X and Y are each independently $OR^1$ or $NHR^2$ wherein $R^1$ and $R^2$ are each independently a hydrogen atom or a $C_{1-22}$ alkyl group, or an optionally modified amino acid residue, or X and Y in combination optionally form —O—.

The "$C_{1-22}$ alkyl group" for $R^1$ or $R^2$ is preferably a $C_{1-6}$ alkyl group, more preferably a methyl group, an ethyl group, or an isopropyl group, still more preferably an ethyl group.

The "optionally modified amino acid residue" for X or Y means a group obtained by removal of one hydrogen atom from the amino group of the "optionally modified amino acid". Examples of the "amino acid" of the "optionally modified amino acid" include α-amino acids, β-amino acids, γ-amino acids, and the like, and α-amino acids are preferable. Cyclic amino acids such as proline and the like are encompassed in the "amino acid". When the "amino acid" is L-form or D-form, all isomers and a mixture thereof are also encompassed in the above-mentioned "amino acid". The "amino acid" is preferably glycine, alanine, valine, or the like, more preferably glycine or alanine, still more preferably glycine.

The above-mentioned "amino acid" is optionally modified at any position. The "modified amino acid residue" is preferably a carboxyl group-modified amino acid residue, more preferably an amino acid residue wherein the carboxyl group is esterified by a $C_{1-22}$ alkoxy group (preferably a methoxy group, an ethoxy group) or amidated by a $C_{1-22}$ alkylamino group.

The "optionally modified amino acid residue" is preferably a group derived from glycine ethyl ester, glycine methyl ester, or alanine methyl ester.

X is preferably $OR^1$ wherein $R^1$ is as defined above, or an optionally modified amino acid residue;

more preferably $OR^1$ wherein $R^1$ is as defined above, or an α-amino acid residue wherein the carboxyl group is esterified by a $C_{1-22}$ alkoxy group or amidated by a $C_{1-22}$ alkylamino group; further more preferably $OR^1$ wherein $R^1$ is as defined above, or an α-amino acid residue wherein the carboxyl group is esterified by a $C_{1-22}$ alkoxy group (preferably a methoxy group, an ethoxy group);

still more preferably $OR^{1'}$ wherein $R^{1'}$ is a hydrogen atom or a $C_{1-6}$ alkyl group (preferably a methyl group, an ethyl group, an isopropyl group), or an α-amino acid residue (preferably glycine, alanine) wherein the carboxyl group is esterified by a $C_{1-6}$ alkoxy group (preferably a methoxy group, an ethoxy group);

particularly preferably a hydroxyl group, a methoxy group, an ethoxy group, an isopropoxy group, or a group derived from glycine methyl ester, glycine ethyl ester or alanine methyl ester, particularly a hydroxyl group or a methoxy group.

Y is preferably $OR^1$ wherein $R^1$ is as defined above, more preferably $OR^{1'}$ wherein $R^{1'}$ is as defined above, further more preferably a hydroxyl group, a methoxy group or an ethoxy group, still more preferably a hydroxyl group or a methoxy group.

Alternatively, preferably, X and Y in combination optionally form —O—.

Z is a hydrogen atom or a $C_{1-22}$ alkyl group.

The "$C_{1-22}$ alkyl group" for Z is preferably a $C_{1-6}$ alkyl group, more preferably a methyl group.

Z is preferably a hydrogen atom or a $C_{1-6}$ alkyl group, more preferably a hydrogen atom or a methyl group.

W is a $C_{1-22}$ alkyl group, a $C_{1-22}$ alkoxy group or a $C_{1-22}$ alkylamino group.

The "$C_{1-22}$ alkyl group" for W is preferably a $C_{1-16}$ alkyl group, more preferably a methyl group, a nonyl group or a pentadecyl group, still more preferably a methyl group.

The "$C_{1-22}$ alkoxy group" for W is preferably a $C_{1-6}$ alkoxy group, more preferably a tert-butoxy group.

The "$C_{1-22}$ alkylamino group" for W is preferably a $C_{1-6}$ alkylamino group.

W is preferably a $C_{1-22}$ alkyl group or a $C_{1-22}$ alkoxy group, more preferably a $C_{1-16}$ alkyl group or a $C_{1-6}$ alkoxy group, still more preferably a methyl group, a nonyl group, a pentadecyl group or a tert-butoxy group, particularly preferably a methyl group or a tert-butoxy group.

The cysteine derivative represented by the formula (I) is preferably a cysteine derivative wherein X is $OR^1$ wherein $R^1$ is as defined above, or an optionally modified amino acid residue, Y is $OR^1$ wherein $R^1$ is as defined above, or X and Y in combination optionally form —O—, Z is a hydrogen atom or a $C_{1-22}$ alkyl group, and W is a $C_{1-22}$ alkyl group or a $C_{1-22}$ alkoxy group, more preferably a cysteine derivative wherein X is $OR^1$ wherein $R^1$ is as defined above, or an α-amino acid residue wherein the carboxyl group is esterified by a $C_{1-22}$ alkoxy group or amidated by a $C_{1-22}$ alkylamino group, Y is $OR^1$ wherein $R^1$ is as defined above, or X and Y in combination optionally form —O—, Z is a hydrogen atom or a $C_{1-22}$ alkyl group, and W is a $C_{1-22}$ alkyl group or a $C_{1-22}$ alkoxy group, further more preferably a cysteine derivative wherein X is $OR^1$ wherein $R^1$ is as defined above, or an α-amino acid residue wherein the carboxyl group is esterified by a $C_{1-22}$ alkoxy group, Y is $OR^1$ wherein $R^1$ is as defined above, or X and Y in combination optionally form —O—, Z is a hydrogen atom or a $C_{1-22}$ alkyl group, and W is a $C_{1-22}$ alkyl group or a $C_{1-22}$ alkoxy group, still more preferably a cysteine derivative wherein X is $OR^{1'}$ wherein $R^{1'}$ is a hydrogen atom or a $C_{1-6}$ alkyl group, or a α-amino acid residue (preferably glycine, alanine) wherein the carboxyl group is esterified by a $C_{1-6}$ alkoxy group (preferably a methoxy group, an ethoxy group), Y is $OR^{1'}$ wherein $R^{1'}$ is a hydrogen atom or a $C_{1-6}$ alkyl group, or X and Y in combination optionally form —O—, Z is a hydrogen atom or a $C_{1-6}$ alkyl group, and W is a $C_{1-16}$ alkyl group or a $C_{1-6}$ alkoxy group, particularly preferably a cysteine derivative wherein X is a hydroxyl group, a methoxy group, an ethoxy group, an isopropoxy group, or a group derived from glycine methyl ester, glycine ethyl ester or alanine methyl ester, Y is a hydroxyl group, a methoxy group or an ethoxy group, or X and Y in combination optionally form —O—, Z is a hydrogen atom or a methyl group, and W is a methyl group, a nonyl group, a pentadecyl group or a tert-butoxy group.

Specifically, N-acetyl-2-methylthiazolidine-2,4-dicarboxylic acid, and N-acetyl-2-methylthiazolidine-2,4-dicarboxylic acid 2-ethyl ester are preferable, and N-acetyl-2-methylthiazolidine-2,4-dicarboxylic acid 2-ethyl ester is more preferable.

The above-mentioned cysteine derivative represented by formula (I) (N-acetyl-2-methylthiazolidine-2,4-dicarboxylic acid and N-acetyl-2-methylthiazolidine-2,4-dicarboxylic acid anhydride are excluded) is a novel compound.

Each substituent in the above-mentioned formula (IX) is explained in the following.

X' is $OR^1$ or $NHR^2$ wherein $R^1$ and $R^2$ are each independently a hydrogen atom or a $C_{1-22}$ alkyl group, or an optionally modified amino acid residue.

Examples of the "$OR^1$", "$NHR^2$", and "optionally modified amino acid residue" for X' include those similar to the aforementioned "$OR^1$", "$NHR^2$", and "optionally modified amino acid residue" for X or Y.

X' is preferably OR' wherein $R^1$ is as defined above, more preferably $OR^{1'}$ wherein $R^{1'}$ is a hydrogen atom or a $C_{1-6}$ alkyl group (preferably a methyl group), still more preferably a hydroxyl group or a methoxy group.

D is (1) an aromatic heterocyclic group optionally substituted by substituent(s) selected from
 (i) a hydroxyl group, and
 (ii) a $C_{1-6}$ alkyl group optionally substituted by hydroxyl group(s), or (2) a $C_{1-22}$ alkyl group optionally substituted by hydroxyl group(s).

Examples of the "aromatic heterocyclic group" of the "aromatic heterocyclic group optionally substituted by substituent(s) selected from (i) a hydroxyl group, and (ii) a $C_{1-6}$ alkyl group optionally substituted by hydroxyl group(s)" for D include a 4- to 7-membered (preferably a 5- or 6-membered) monocyclic aromatic heterocyclic group containing, as a ring-constituting atom besides carbon atoms, 1 to 4 hetero atoms selected from an oxygen atom, a sulfur atom (the sulfur atom is optionally oxidized) and a nitrogen atom, and fused aromatic heterocyclic group. Examples of the fused aromatic heterocyclic group include a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are condensed, and the like.

Preferable examples of the aromatic heterocyclic group include monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,5-oxadiazol-3-yl, 1,3,4-oxadiazol-2-yl), thiadiazolyl (e.g., 1,2,3-thiadiazol-4-yl, 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-3-yl, 1,2,4-triazin-5-yl, 1,2,4-triazin-6-yl), and the like;

fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl, 4-benzofuranyl, 5-benzofuranyl, 6-benzofuranyl, 7-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl, 6-benzothiazolyl), benzimidazolyl (e.g., benzimidazol-1-yl, benzimidazol-2-yl, benzimidazol-5-yl), benzotriazolyl (e.g., 1H-1,2,3-benzotriazol-1-yl, 1H-1,2,3-benzotriazol-5-yl), indolyl (e.g., indol-1-yl, indol-2-yl, indol-3-yl, indol-5-yl), indazolyl (e.g., 2H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), thienopyrazolyl (e.g., 1H-thieno[2,3-c]pyrazol-5-yl), pyrazolotriazinyl (e.g., pyrazolo[5,1-c][1,2,4]triazin-3-yl), triazolopyrimidinyl (e.g., [1,2,4]triazolo[1,5-a]pyrimidin-2-yl), phthalazinyl, and the like; and the like. The aromatic heterocyclic group is preferably a monocyclic aromatic heterocyclic group, more preferably pyridyl (preferably 4-pyridyl).

The "aromatic heterocyclic group" optionally has substituent(s) selected from (i) a hydroxyl group, and
(ii) a $C_{1-6}$ alkyl group (preferably a methyl group) optionally substituted by hydroxyl group(s), at any substitutable position. While the number of the substituents is not particularly limited, it is preferably 1 to 6, more preferably 1 to 4, still more preferably 1 to 3. When the number of the substituents is 2 or more, the respective substituents may be the same or different.

The "aromatic heterocyclic group optionally substituted by substituent(s) selected from (i) a hydroxyl group, and (ii) a $C_{1-6}$ alkyl group optionally substituted by hydroxyl group(s)" for D is preferably an aromatic heterocyclic group optionally substituted by 1 to 6 substituents selected from (i) a hydroxyl group, and (ii) a $C_{1-6}$ alkyl group optionally substituted by hydroxyl group(s), more preferably a monocyclic aromatic heterocyclic group [preferably pyridyl (preferably 4-pyridyl)] optionally substituted by 1 to 4 substituents selected from (i) a hydroxyl group, and (ii) a $C_{1-6}$ alkyl group optionally substituted by hydroxyl group(s), still more preferably a monocyclic aromatic heterocyclic group [preferably pyridyl (preferably 4-pyridyl)] optionally substituted by 1 to 4 (preferably 1 to 3) substituents selected from a hydroxyl group, a methyl group and a hydroxymethyl group, particularly preferably 3-hydroxy-5-(hydroxymethyl)-2-methylpyridin-4-yl.

The "$C_{1-22}$ alkyl group" of the "$C_{1-22}$ alkyl group optionally substituted by hydroxyl group(s)" for D is preferably a $C_{1-16}$ alkyl group, more preferably a $C_{1-6}$ alkyl group, particularly preferably a pentyl group.

The "$C_{1-22}$ alkyl group" optionally has hydroxyl group(s) at any substitutable position. While the number of the hydroxyl groups is not particularly limited, it is preferably 1 to 16, more preferably 1 to 10, still more preferably 1 to 6, particularly preferably 1 to 5.

The "$C_{1-22}$ alkyl group" of the "$C_{1-22}$ alkyl group optionally substituted by hydroxyl group(s)" for D is preferably a $C_{1-22}$ alkyl group optionally substituted by 1 to 16 hydroxyl groups, more preferably a $C_{1-16}$ alkyl group optionally substituted by 1 to 10 hydroxyl groups, still more preferably a $C_{1-6}$ alkyl group (preferably pentyl group) optionally substituted by 1 to 6 (preferably 1 to 5) hydroxyl groups, particularly preferably 1,2,3,4,5-pentahydroxypentyl.

D is preferably
(1) an aromatic heterocyclic group optionally substituted by 1 to 6 substituents selected from
  (i) a hydroxyl group, and
  (ii) a $C_{1-6}$ alkyl group optionally substituted by hydroxyl group(s), or
(2) a $C_{1-22}$ alkyl group optionally substituted by 1 to 16 hydroxyl groups,
more preferably
(1) a monocyclic aromatic heterocyclic group [preferably pyridyl (preferably 4-pyridyl)] optionally substituted by 1 to 4 substituents selected from
  (i) a hydroxyl group, and
  (ii) a $C_{1-6}$ alkyl group optionally substituted by hydroxyl group(s), or
(2) a $C_{1-16}$ alkyl group, optionally substituted by 1 to 10 hydroxyl groups
still more preferably
(1) a monocyclic aromatic heterocyclic group [preferably pyridyl (preferably 4-pyridyl)] optionally substituted by 1 to 4 (preferably 1 to 3) substituents selected from a hydroxyl group, a methyl group and a hydroxymethyl group, or
(2) a $C_{1-6}$ alkyl group (preferably pentyl group) optionally substituted by 1 to 6 (preferably 1 to 5) hydroxyl groups, particularly preferably
(1) 3-hydroxy-5-(hydroxymethyl)-2-methylpyridin-4-yl, or
(2) 1,2,3,4,5-pentahydroxypentyl.
Z' is a hydrogen atom or a $C_{1-22}$ alkyl group.
Z' is preferably a hydrogen atom.
W' is a $C_{1-22}$ alkyl group, a $C_{1-22}$ alkoxy group or a alkylamino group.
W' is preferably a $C_{1-22}$ alkyl group, more preferably a $C_{1-16}$ alkyl group, still more preferably a $C_{1-6}$ alkyl group, particularly preferably a methyl group.

The cysteine derivative represented by formula (IX) is preferably a cysteine derivative wherein
X' is $OR^1$ wherein $R^1$ is as defined above,
D is
(1) an aromatic heterocyclic group optionally substituted by 1 to 6 substituents selected from
  (i) a hydroxyl group, and
  (ii) a $C_{1-6}$ alkyl group optionally substituted by hydroxyl group(s), or
(2) a $C_{1-22}$ alkyl group optionally substituted by 1 to 16 hydroxyl groups,
Z' is a hydrogen atom, and
W' is a $C_{1-22}$ alkyl group,
  more preferably a cysteine derivative wherein X' is $OR^{1'}$ wherein $R^{1'}$ is a hydrogen atom or a $C_{1-6}$ alkyl group (preferably a methyl group),
D is
(1) a monocyclic aromatic heterocyclic group [preferably pyridyl (preferably 4-pyridyl)] optionally substituted by 1 to 4 substituents selected from
  (i) a hydroxyl group, and
  (ii) a $C_{1-6}$ alkyl group optionally substituted by hydroxyl group(s), or
(2) a $C_{1-16}$ alkyl group optionally substituted by 1 to 10 hydroxyl groups,
Z' is a hydrogen atom, and
W' is a $C_{1-16}$ alkyl group,
  still more preferably a cysteine derivative wherein X' is $OR^{1'}$ wherein $R^{1'}$ is a hydrogen atom or a $C_{1-6}$ alkyl group (preferably a methyl group),
D is
(1) a monocyclic aromatic heterocyclic group [preferably pyridyl (preferably 4-pyridyl)] optionally substituted by 1 to 4 (preferably 1 to 3) substituents selected from a hydroxyl group, a methyl group and a hydroxymethyl group, or
(2) a $C_{1-6}$ alkyl group (preferably pentyl group) optionally substituted by 1 to 6 (preferably 1 to 5) hydroxyl groups,
Z' is a hydrogen atom, and
W' is a $C_{1-6}$ alkyl group (preferably a methyl group),
  particularly preferably a cysteine derivative wherein X' is a hydroxyl group or a methoxy group,
D is
(1) 3-hydroxy-5-(hydroxymethyl)-2-methylpyridin-4-yl, or
(2) 1,2,3,4,5-pentahydroxypentyl,
Z' is a hydrogen atom, and
W' is a methyl group.

Specifically, N-acetyl-2-[3-hydroxy-5-(hydroxymethyl)-2-methylpyridin-4-yl]thiazolidine-4-carboxylic acid, N-acetyl-2-(1,2,3,4,5-pentahydroxypentyl)thiazolidine-4-carboxylic acid methyl ester and N-acetyl-2-(1,2,3,4,5-pentahydroxypentyl)thiazolidine-4-carboxylic acid are preferable.

The cysteine derivative represented by formula (I) or a salt thereof, and the cysteine derivative represented by formula (IX) or a salt thereof are collectively referred to as "the cysteine derivative of the present invention".

While the cysteine derivative of the present invention contains (2R,4R)-form, (2S,4S)-form, (2R,4S)-form and (2S,4R)-form based on the asymmetric carbon atoms at the 2-position and 4-position of the thiazolidine ring, all such isomers and mixtures thereof are encompassed in the cysteine derivative of the present invention (excluding compound wherein D and Z' are the same). In the present specification, (2R,4R)-form, (2S,4S)-form and a mixture thereof are referred to as the cis form, and (2R,4S)-form, (2S,4R)-form and a mixture thereof are sometimes referred to as the trans form.

The cysteine derivative of the present invention is preferably a trans form from the aspect of stability. Particularly, the trans form of the cysteine derivative of the present invention is superior in the preservation stability under acidic conditions (e.g., pH 5 or below (preferably pH 4 or below)), and therefore, is highly useful when added to cosmetic agents such as a whitening agent and the like having such a pH.

Particularly, the cysteine derivative of the present invention is preferably a trans form of N-acetyl-2-methylthiazolidine-2,4-dicarboxylic acid or a salt thereof (i.e., (2S,4R)—N-acetyl-2-methylthiazolidine-2,4-dicarboxylic acid, (2R,4S)—N-acetyl-2-methylthiazolidine-2,4-dicarboxylic acid, or a mixture thereof, or a salt thereof); a trans form of N-acetyl-2-methylthiazolidine-2,4-dicarboxylic acid 2-ethyl ester or a salt thereof (i.e., (2S,4R)—N-acetyl-2-methylthiazolidine-2,4-dicarboxylic acid 2-ethyl ester, (2R,4S)—N-acetyl-2-methylthiazolidine-2,4-dicarboxylic acid 2-ethyl ester, or a mixture thereof, or a salt thereof), more preferably a trans form of N-acetyl-2-methylthiazolidine-2,4-dicarboxylic acid 2-ethyl ester or a salt thereof.

Examples of the salt of the cysteine derivative include salts with an inorganic base, salts with an organic base, salts with an amino acid, and the like.

Examples of the salt with an inorganic base include a sodium salt, potassium salt, calcium salt, magnesium salt, ammonium salt, and the like.

Examples of the salt with an organic base include salts with methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, choline, cinchonine, meglumine, and the like.

Examples of the salt with an amino acid include salts with lysine, arginine, and histidine.

Each salt can be obtained by reacting the cysteine derivative of the present invention with an inorganic base, an organic base. or an amino acid according to a method known per se.

The cysteine derivative of the present invention can be used as a cysteine prodrug. In the present specification, the term "cysteine prodrug" refers to a compound having improved stability and the like by modifying cysteine, which is enzymatically or non-enzymatically decomposed, and converted to cysteine or a compound having a sulfanyl group which shows physiological activity in the living body. Therefore, the cysteine derivative of the present invention can be used as a substitute for cysteine as long as it is effectively converted to cysteine or a compound having a sulfanyl group in the system.

In one embodiment of the present invention, the cysteine derivative of the present invention can be used as an eumelanin production suppressing agent, a whitening agent, or a pigmented spot-preventing or treating agent. These applications utilize properties of the cysteine derivative of the present invention, where it maintains a stable dosage form but is decomposed into cysteine comparatively rapidly due to an enzyme such as acylase and the like at an action site via skin absorption.

In another embodiment of the present invention, the cysteine derivative of the present invention can be added to various cosmetic agents or skin external preparations. The cosmetic agent and the skin external preparation of the present invention may take any form and are free of any particular limitation. They can be in any form such as solution, paste, gel, solid, powder and the like. Specific examples thereof include skin lotion, toner, cream, skin milk, serum, shampoo, hair rinse, conditioner, enamel, foundation, eyeliner, eyebrow pencil, mascara, chapstick, face powder, powder, facial mask, perfume, cologne, cleansing foam, cleansing oil, cleansing gel, dentifrice, soap, aerosol, bath agent, hair-growth promoter, and sun protectant.

When the cysteine derivative of the present invention is added to a cosmetic agent or skin external preparation, the lower limit value of addition is not particularly limited as long as its effect can be exhibited. It is preferably 0.0001 wt %, based on the total weight of the cosmetic agent or skin external preparation. For a sufficient effect to be exhibited, it is more preferably 0.001 wt %, further more preferably 0.01 wt %, still more preferably 0.1 wt %, especially preferably 0.5 wt %, particularly preferably 1 wt %, based on the total weight of the cosmetic agent or skin external preparation.

When the cysteine derivative of the present invention is added to a cosmetic agent or skin external preparation, the upper limit value of addition is not particularly limited as long as its effect can be exhibited. It is preferably 20 wt %, based on the total weight of the cosmetic agent or skin external preparation. It is more preferably 18 wt %, further more preferably 16 wt %, still more preferably 14 wt %, especially preferably 12 wt %, and particularly preferably 10 wt %, based on the total weight of the cosmetic agent or skin external preparation.

When a cosmetic composition or whitening composition of the present invention is to be provided, various components (for example a cosmetically acceptable carrier), generally usable for cosmetic composition, skin external preparations and quasi-drugs may be added, in addition to the cysteine derivative of the present invention, within the range not inhibiting the effect of the invention.

The cosmetically acceptable carrier include for example, oily component, surfactant, amino acids, amino acid derivatives, lower alcohol, polyhydric alcohol, sugar alcohol and alkylene oxide adduct thereof, water-soluble polymer, antimicrobial agent and disinfectant, anti-inflammatory agent, analgesic, antifungal agent, stratum corneum softening and peeling agent, skin colorant, hormone, UV absorber, hair-growth promoter, whitening agent, antiperspirant and astringent active ingredient, perspiration deodorant, vitamin, vasodilator, crude drug, pH adjuster, viscosity modifier, pearly pigment, natural perfume, synthetic perfume, dye, antioxidant, preservative, emulsifier, fat and wax, silicone compound, balm, and the like.

Examples of the oily component include saturated or unsaturated fatty acid and higher alcohols obtained therefrom, straight chain or branched chain fatty alcohol esters such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate, erucyl erucate and the like, squalane, squalene, castor oil and/or hydrogenated castor oil and a derivative thereof, glycerides such as hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, tartaric acid monoglyceride, tartaric acid diglyceride, citric acid monoglyceride, citric acid diglyceride, malic acid monoglyceride, malic acid diglyceride and ethylene oxide 1-30 mol adduct of these glycerides, and the like, beeswax, lanolins including liquid and purified lanolin and a derivative thereof, oily starting materials derived from animals and plants such as almond oil, avocado oil, olive oil, rape seed oil, coconut oil, macadamia nut oil, jojoba oil, carnauba wax, sesame oil, cacao oil, palm oil, mink oil, Japan wax, candelilla wax, whale wax and the like, oily starting materials derived from petroleum and mineral such as paraffin, microcrystalline wax, liquid paraffin, petrolatum, ceresin and the like, silicons such as silicone polymers including methylpolysiloxane, polyoxyethylene.methylpolysiloxane, polyoxypropylene.methylpolyoxysiloxane, poly(oxyethylene, oxypropylene).methylpolysiloxane, methylphenylpolysiloxane, fatty acid modified polysiloxane, aliphatic alcohol modified polysiloxane, amino acid modified polysiloxane and the like, and the like, resin acid, fatty acid ester, ketones, and the like.

Examples of the surfactant include anion surfactants, for example, N-long chain acylamino acid salts such as N-long chain acyl acidic amino acid salts (e.g., N-long chain acylglutamic acid salt, N-long chain acylaspartic acid salt and the like), N-long chain acyl neutral amino acid salts (e.g., N-long chain acylglycine salt, N-long chain acylalanine salt, N-long chain acyltreonine salt and the like) and the like, N-long chain fatty acid acyl-N-methyltaurine salt, alkylsulfate and alkylene oxide adduct thereof, fatty acid amide ether sulfate, metal salt and weak basic salt of fatty acid, sulfosuccinic acid type surfactant, alkylphosphate and alkylene oxide adduct thereof, alkylethercarboxylic acid and the like; non-ionic surfactants, such as ether type surfactants (e.g., glycerolether and alkylene oxide adduct thereof and the like), ester type surfactants (e.g., glycerol ester and alkylene oxide adduct thereof and the like), ether ester type surfactants (e.g., sorbitan ester and alkylene oxide adduct thereof and the like), ester type surfactants (e.g., polyoxyalkylene fatty acid ester, glycerol ester, fatty acid polyglycerol ester, acylamino acid polyglycerol ester, sorbitan ester, sucrose fatty acid ester and the like), alkyl glucosides, nitrogen-containing type non-ionic surfactants (e.g., hydrogenated castor oil pyroglutamic acid diester and ethylene oxide adduct thereof, as well as fatty acid alkanolamide and the like), and the like; cation surfactants such as aliphatic amine salts (e.g., alkylammonium chloride, dialkylammonium chloride and the like), quaternary ammonium salts thereof, aromatic quaternary ammonium salts (e.g., benzalkonium salt and the like), fatty acid acylarginine ester, alkyloxyhydroxypropylarginine salt and the like; and betaine type surfactants such as alkylbetaine, alkylamidebetaine, aminopropionate, carboxybetaine and the like, ampholytic surfactants such as aminocarboxylic acid type surfactant, imidazoline type surfactant and the like, and the like.

Examples of the amino acids include glycine, alanine, serine, threonine, arginine, glutamic acid, aspartic acid, leucine, valine, and the like.

Examples of the amino acid derivative include pyrrolidonecarboxylic acid and a salt thereof, trimethylglycine, lauroyllysine, and the like.

Examples of the lower alcohol include ethanol, propanol, isopropanol, butanol, and the like.

Examples of the polyhydric alcohol include glycerol, diglycerol, ethylene glycol, 1,3-butylene glycol, propylene glycol, isoprene glycol, and the like.

Examples of the sugar alcohol and an alkylene oxide adduct thereof include mannitol, erythritol, and the like.

Examples of the water-soluble polymer include polyamino acids including polyglutamic acid and polyaspartic acid, and a salt thereof, polyethylene glycol, gum arabics, alginates, xanthan gum, hyaluronic acid, hyaluronic acid salts, chitin, chitosan, aqueous chitin, carboxyvinyl polymer, carboxymethylcellulose, hydroxyethylcellulose, polyacrylamide, polyvinyl alcohol, polyvinylpyrrolidone, hydroxypropyltrimethylammonium chloride, polydimethylmethylenepiperidium chloride, polyvinylpyrrolidone derivative quaternary ammonium, cationated protein, collagen decomposition product and a derivative thereof, acylated protein, polyglycerol, and the like.

Examples of the antimicrobial agent and disinfectant include 4-hydroxybenzoic acid and a salt thereof and ester thereof, triclosan, chlorhexidine, phenoxyethanol, menthol, mint oil, glyceryl caprate, glyceryl caprylate, salicylic acid-N-alkylamide, and the like.

Examples of the anti-inflammatory agent, analgesic, antifungal agent, stratum corneum softening and peeling agent, skin colorant and hormone include Japanese cypress thiol, hydrocortisone(V), ε-aminocarboxylic acid, azulene, allantoin, glycyrrhizic acid derivative, β-glycyrrhetinic acid, and the like.

The UV absorber is, for example, an organic substance (photoprotective filter) which is liquid or crystal at room temperature, and can absorb ultraviolet rays and release the absorbed energy as radiation having a longer wavelength (for example, heat). Examples thereof include UV-B filter and UV-A filter. The UV-B filter can be oil-soluble or water-soluble. Examples of the oil-soluble substance include 3-benzylidenecamphor or 3-benzylidenenorcamphor and a derivative thereof (e.g., 3-(4-methylbenzylidene)-camphor); 4-aminobenzoic acid derivative (preferably 4-(dimethylamino)-benzoic acid-2-ethylhexyl ester, 4-(dimethylamino)-benzoic acid-2-octyl ester, 4-(dimethylamino)-benzoic acid pentyl ester); cinnamic acid ester (preferably 4-methoxycinnamic acid-2-ethylhexyl ester, 4-methoxycinnamic acid propyl ester, 4-methoxycinnamic acid isopentyl ester, 2-cyano-3,3-phenylcinnamic acid-2-ethylhexyl ester (Octocrylene)); salicylic acid ester (preferably salicylic acid-2-ethylhexyl ester, salicylic acid-4-isopropylbenzyl ester, salicylic acid homomenthyl ester); benzophenone derivative (preferably 2-hydroxy-4-methoxybenzophenone, 2-hydroxy-4-methoxy-4'-methylbenzophenone, 2,2'-dihydroxy-4-meth- oxybenzophenone); benzalmalonic acid ester (preferably 4-methoxybenzalmalonic acid di-2-ethylhexyl ester); triazine derivative (e.g., 2,4,6-trianilino-(p-carbo-2'-ethyl-1'-hexyloxy)-1,3,5-triazine, octyl.triazone, dioctyl.butamide.triazone (Uvasorb (registered trade mark) HEB)); propane-1,3-dione (e.g., 1-(4-t-butylphenyl)-3-(4'-methoxyphenyl)-propane-1,3-dione); ketotricyclo(5.2.1.0)decane derivative, and the like. Examples of the water-soluble substance include 2-phenylbenzimidazole-5-sulfonic acid and alkali metal salt, alkaline earth metal salt, ammonium salt, alkylammonium salt, alkanolammonium salt and glucammonium salt thereof; sulfonic acid derivative of benzophenone (preferably 2-hydroxy-4-methoxybenzophenone-5-sulfonic acid and a salt thereof); sulfonic acid derivative of 3-benzylidenecamphor (e.g., 4-(2-oxo-3-bornylidenemethyl)-benzenesulfonic acid and 2-methyl-5-(2-oxo-3-bornylidene)-sulfonic acid and a salt thereof, and the like. As the UV-A filter, a benzoylmethane derivative is particularly used and, for example, 1-(4'-t-butylphenyl)-3-(4'-methoxyphenyl)-propane-1,3-dione, 4-t-butyl-4'-methoxydibenzoylmethane (Parsol (registered trade mark) 1789), 1-phenyl-3-(4'-isopropylphenyl)-propane-1,3-dione, enamine compound, and the like can be mentioned.

Examples of the hair-growth promoter include pantothenic acid and a derivative thereof, placenta extract, allantoin, and the like.

Examples of the whitening agent include arbutin, kojic acid, vitamin C and a derivative thereof, and the like.

Examples of the antiperspirant and astringent active ingredient, and perspiration deodorant include salts of aluminum, zirconium and zinc such as aluminum chloride, aluminum chlorohydrate, aluminum zirconium trichlorohydrate, aluminum zirconium tetrachlorohydrate, zinc pyrrolidonecarboxylate, and the like.

Examples of the vitamin include vitamins A, $B_1$, $B_2$, $B_6$, E and derivatives thereof, and the like.

Examples of the vasodilator include swertia japonica extract, cepharanthine, and the like.

Examples of the crude drug include apricot extract, avocado extract, aloe extract, turmeric extract, orange extract, chamomilla extract, kiwi extract, ginkgo extract, tea extract, sage extract, swertia japonica extract, Persicae Semen extract, rose extract, sunflower extract, grape extract, loofah extract, peach leaf extract, eucalyptus extract, lavender extract, green tea extract, apple extract, lemon extract, rosemary extract, and the like.

Examples of the pH adjuster include citric acid, adipic acid, ascorbic acid, phosphoric acid, glutamic acid, lactic acid, sulfuric acid, hydrochloric acid, ammonium, sodium hydroxide, potassium hydroxide, arginine, hydroquinone and a derivative thereof, γ-oryzanol, and the like.

Examples of the viscosity modifier include agar, organic modified clay mineral and the like.

Examples of the pearly pigment include alkyleneglycol ester, fatty acid alkanolamide, fatty acid monoglyceride, fatty ether, and the like.

Examples of the natural perfume include flavor extracted from flowers (lily, lavender, rose, jasmine, etc.), stem and leaf (geranium, patchouli, etc.), fruit and fruit skin (lemon, orange, anise) and the like, and the like.

Examples of the synthetic perfume include ester, ether, aldehyde, ketone, alcohol and hydrocarbon type flavor, and the like.

Examples of the dye include cochineal red A (C.I.16255), patent blue (C.I.42051), chlorophyllin (C.I.75810), and the like.

Examples of the antioxidant include tocopherol, sodium sulfite, and the like.

Examples of the preservative include phenoxyethanol, paraben, pentanediol, and the like.

The emulsifier is, for example, a nonionic surfactant, and examples thereof include an addition resultant product of 2 to 30 mol of ethylene oxide and/or 0 to 5 mol of propylene oxide to straight chain fatty alcohol having 8 to 22 carbon atoms, fatty acid having 12 to 22 carbon atoms, alkylphenol wherein alkyl group has 8 to 15 carbon atoms, or alkylamine wherein alkyl group has 8 to 22 carbon atoms; alkyl and/or alkenyl oligoglycoside wherein alkyl(alkenyl) group has 8 to 22 carbon atoms, and an ethoxylated product thereof; ethylene oxide (1 to 15 mol) adduct of castor oil and/or hydrogenated castor oil; ethylene oxide (15 to 60 mol) adduct of castor oil and/or hydrogenated castor oil; partial ester of unsaturated straight chain or saturated branched fatty acid having 12 to 22 carbon atoms and/or hydroxycarboxylic acid having 3 to 18 carbon atoms and glycerol and/or sorbitan, and adduct thereof with 1 to 30 mol of ethylene oxide; partial ester of polyglycerol (2 to 8 average degree of self-condensation), polyethylene glycol (molecular weight 400 to 5000), trimethylolpropane, pentaerythritol, sugar alcohol (for example, sorbitol), alkyl glucoside (for example, methyl glucoside, butyl glucoside, lauryl glucoside) and/or polyglucoside (for example, cellulose), and saturated and/or unsaturated straight chain or branched fatty acid having 12 to 22 carbon atoms and/or hydroxycarboxylic acid having 3 to 18 carbon atoms, and adduct thereof with 1 to 30 mol of ethylene oxide; mixed ester of pentaerythritol, fatty acid, mixed ester of citric acid and fatty alcohol, and/or fatty acid having 6 to 22 carbon atoms, and methyl glucose and polyol (preferably glycerol or polyglycerol); mono-, di-, trialkylphosphate and mono-, di- and/or tri-PEG-alkylphosphate and a salt thereof; wool wax alcohol; polysiloxane/polyalkyl/polyether copolymer and the corresponding derivative; block copolymer (e.g., polyethylene glycol-30 dipolyhydroxystearate); polymer emulsifier (e.g., Goodrich Pemulen type (TR-1, TR-2)); polyalkylene glycol, and glycerol carbonate and the like. Examples of ethylene oxide adduct include ethylene oxide of fatty alcohol, fatty acid, alkylphenol or castor oil, and examples of propylene oxide adduct include known, commercially available products. Examples of partial glyceride include hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and the like. Moreover, ethylene oxide 1 to 30 mol (preferably 5 to 10 mol) adduct of the above-mentioned partial glyceride is also suitable. Examples of sorbitan ester include sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinolate, sorbitan sesquiricinolate, sorbitan diricinolate, sorbitan triricinolate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and industrial mixtures thereof. In addition, ethylene oxide 1 to 30 mol (preferably 5 to 10 mol) adduct of the above-mentioned sorbitan ester is also suitable. Examples of polyglycerol ester include polyglyceryl-2 dipolyhydroxystearate (Dehymuls (registered trade mark) PGPH), polyglyceryl-3 diisostearate (Lameform (registered trade mark) TGI), polyglyceryl-4 isostearate (Isolan (registered trade mark) GI 34), polyglyceryl-3 oleate, diisostearoyl polyglyceryl-3 diisostearate (Isolan (registered trade mark) PDI), polyglyceryl-3 methylglucose distearate (Tego Care (registered trade mark) 450), polyglyceryl-3 beeswax (Cera Bellina (registered trade mark)), polyglyceryl-4 caprate (Polyglycerol Caprate T2010/90), polyglyceryl-3 cetyl ether (Chimexane (registered trade mark) NL), polyglyceryl-3 distearate (Cremophor (registered trade mark) GS 32) and polyglyceryl polyricinolate (Admul (registered trade mark) WOL 1403), polyglyceryl dimerate isostearate, mixtures thereof and the like. Examples of polyol ester include mono-, di- and tri-ester of trimethylolpropane or pentaerythritol and lauric acid, palm oil fatty acid, tallow fatty acid, palmitic acid, stearic acid, oleic acid, behenic acid and the like, which may be reacted with ethylene oxide (1 to 30 mol) where necessary.

Examples of the fat and wax include 12-hydroxystearic acid, lanolin, beeswax, candelilla wax, carnauba wax and the like.

Examples of the silicone compound include dimethylpolysiloxane, methylphenylpolysiloxane, cyclic silicone, amino-, fatty acid-, alcohol-, polyether-, epoxy-, fluorine-, glycoside- and/or alkyl-modified silicone compound (which can be liquid or resin-like at room temperature), simethicone which is a mixture of dimethicone having an average chain length of dimethyl siloxane unit number of 200 to 300 and silicate hydride, and the like.

Examples of the balm include a mixture of natural and synthetic flavor. Examples of the natural flavor include plant-derived starting materials such as flower (lily, lavender, rose, jasmine, neroli, ylang-ylang), stem and leaf (geranium, patchouli, petitgrain), fruit (anise, cilantro, caraway, juniper), fruit skin (bergamot, lemon, orange), root (nutmeg, angelica, celery, cardamom, costus, irid, calamus), tree (pine, sandalwood, guaiac, cedar, red sandalwood), herb and grass (tarragon, lemongrass, sage, thyme), acerose leaf and branch (spruce, fir, pine, scrub pine), resin and balsam (galbanum, elemi, benzoin, myrrh, frankincense, opopanax) and the like, and animal-derived starting materials such as civet, beaver, and the like. Examples of the comparatively low volatile essential oil often used as an aromatic component include sage oil, chamomile oil, clove oil, *Melissa officinalis* oil, mint oil, cinnamon leaf oil, lime flower oil, juniper berry oil, vetiver oil, balm, galbanum oil, labdanum oil and lavandin oil, bergamot oil, dihydromyrcenol, lilial, lyral, citronellol, phenylethyl alcohol, α-hexylcinnam aldehyde, geraniol, benzylacetone, cyclamenaldehyde, linalool, Boisambrene Forte, Ambroxan, indole, Hedione, Sandelice, citrus oil, mandarin oil, orange oil, allylpentyl glycholate, Cyclovertal, lavandin oil, clary oil, β-damascone, geranium oil bourbon, cyclohexyl salicylate, Vertofix Coeur, Iso-E-Super, Fixolide NP, evernyl, Iraldein gamma, phenylacetic acid, geranyl acetate, benzyl acetate, rose oxide, Romilat, Irotyl and Floramat, peppermint oil, spearmint oil, anise oil, illicium verum oil, caraway oil, eucalyptus oil, fennel oil, citrus oil, wintergreen oil, clove oil, menthol, and the like.

In another embodiment of the present invention, the cysteine derivative of the present invention may be used as a cysteine substitute for food or drink such as nutritional supplement, supplement, health food, modified powdered milk for infants and the like, or a pharmaceutical product such as infusion, dye deposition improving drug and the like. Besides these, for example, it can also be used as a flavor starting material or an antioxidant. The amount thereof to be added can be appropriately determined as in the case of cosmetic agents.

The production method of the cysteine derivative represented by the above-mentioned formula (I) (hereinafter sometimes to be abbreviated as cysteine derivative (I)) is not particularly limited and known methods can be combined for the production. Specifically, the synthesis is carried out by the following method, but the method is not limited thereto.

Compound (IV) which is a precursor of cysteine derivative (I) can be synthesized according to the following Production Method 1 or 2, and then cysteine derivative (I) can be synthesized Production Method 3. Compound (IV) may or may not be purified as necessary.

Production Method 1.

Method of obtaining compound (IV) by reacting cysteine, or a compound represented by the formula (II) (hereinafter to be abbreviated as compound (II), the same for compounds represented by other formulas), which is obtained by subjecting cysteine to esterification or amidation in advance, with compound (III) and forming a ring:

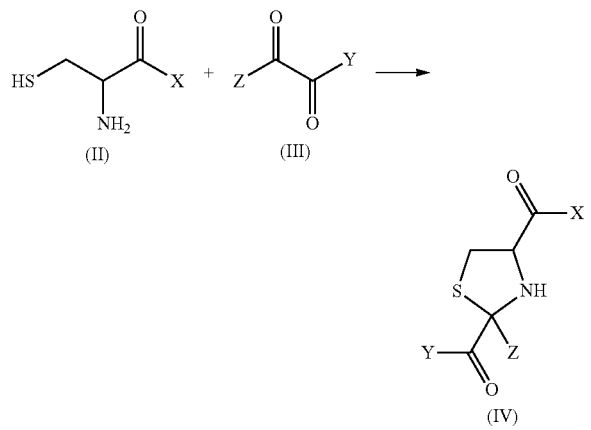

wherein each symbol is as defined above.

Compound (IV) is obtained by reacting compound (II) with compound (III) in water or an alcohol such as methanol, ethanol and the like for 5 to 24 hours. Of compound (II), cysteine ethyl ester can be obtained, for example, by reacting cysteine in the presence of hydrochloric acid or thionyl chloride, in ethyl alcohol, at room temperature for about 5 to 24 hours. Of compound (II), cysteinamide is obtained by reacting a protected cysteine with an amine in the presence of a dehydrating condensing agent such as EDCl HCl (1-ethyl-3-(3-dimethylaminopropyl)-carbodiimide hydrochloride), in a solvent such as methylene chloride and N,N-dimethylformamide (DMF), at room temperature for 5 to 24 hours, and then deprotecting the obtained compound.

Production Method 2.

A method of reacting cysteine (VII) with compound (VIII) to synthesize compound (IV''') which is a thiazolidine derivative, and then, where necessary, subjecting the two carboxyl group of compound (IV''') to esterification or amidation to synthesize compound (IV):

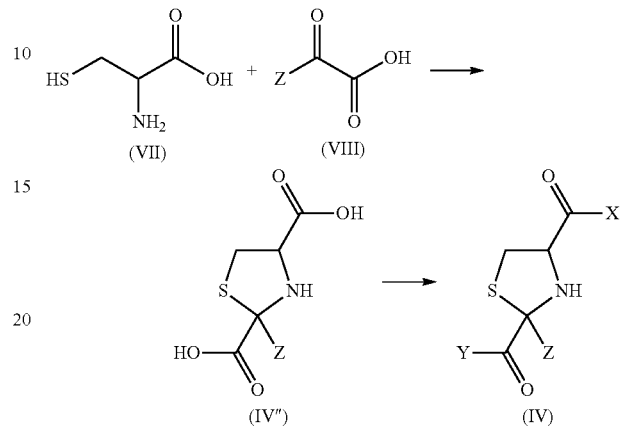

wherein each symbol is as defined above.

Compound (IV) can be obtained by reacting cysteine (VII) with compound (VIII) in water or an alcohol such as methanol, ethanol and the like for 5 to 24 hours to synthesize compound (IV'''), and then, where necessary, reacting the carboxyl group of compound (IV''') under conditions similar to that in the esterification or amidation of cysteine in Production Method 1.

Production Method 3.

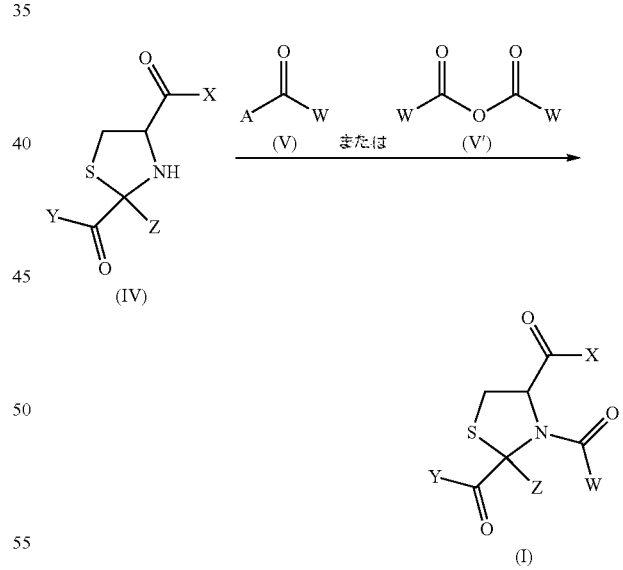

wherein A is a halogen atom, and other symbols are as defined above.

Cysteine derivative (I) can be synthesized by reacting compound (IV) with compound (V) or compound (V') in the presence or absence of a solvent, in the presence or absence of a base. Examples of the solvent include THF (tetrahydrofuran), ethyl acetate, isopropyl acetate, acetonitrile, acetone, ethanol, methanol, dichloromethane, water, a mixture thereof, and the like, and THF, ethyl acetate, isopropyl acetate, acetonitrile, acetone, dichloromethane, water, and a mixture thereof are preferable. Examples of the base include organic bases such as triethylamine, diisopropylethylamine, pyridine, N-methylmorpholine, and the like, inorganic bases such as lithium hydroxide, sodium hydroxide, potassium hydroxide, sodium carbonate, potassium carbonate, sodium acetate, potassium acetate and the like, and triethylamine, diisopropylethylamine, pyridine, N-methylmorpholine, potassium carbonate, sodium carbonate are preferable.

The amount of compound (V) or compound (V') to be used is 1.0 to 5.0 mol, preferably 1.2 to 3.0 mol, per 1 mol of compound (IV). When a base is used, the amount of the base to be used is 1.0 to 5.0 mol, preferably 1.2 to 4.0 mol, per 1 mol of compound (IV). The reaction temperature is −10 to 100° C., preferably 0 to 90° C. The reaction time is 1 hour to 48 hours, preferably 3 hours to 20 hours.

Cysteine derivative (I) may be converted to other cysteine derivative (I) by esterification, amidation, hydrolysis or acid anhydride formation or the like. For example, when X or/and Y is OH, cysteine derivative (I) wherein the carboxyl group is amidated by an optionally modified amino acid residue can be obtained by reacting cysteine derivative (I) with an amino acid, an amino acid ester or a salt thereof (preferably hydrochloride) or an amino acid amide using a dehydrating condensing agent such as EDCI HCl and the like in the presence of a base, as necessary, in an organic solvent. For promotion of the reaction, HOBt H$_2$O (1-hydroxybenzotriazole hydrate) and the like may be added for this reaction. Examples of the base include triethylamine, diisopropylethylamine, and the like. Examples of the organic solvent include dichloromethane, chloroform, THF, DMF, ethyl acetate, and the like. Where necessary, the ester group, amide group or the like of the modified amino acid residue may be deprotected. The reaction conditions of the dehydrating condensation and the like can be conditions generally employed in peptide synthesis.

In addition, by appropriately selecting reaction conditions for the production of cysteine derivative (I) from compound (IV), the trans form or cis form of cysteine derivative (I) can be selectively produced. For example, a) a trans form of cysteine derivative (I) wherein X is a hydroxyl group and Y is a C$_{1-22}$ alkoxy group (i.e., cysteine derivative (I')) can be selectively produced by reacting compound (IV) wherein X is a hydroxyl group and Y is a C$_{1-22}$ alkoxy group (i.e., compound (IV')) with compound (V) in the presence of an organic base, or with compound (V') in the absence of a base, b) a cis form of cysteine derivative (I) wherein X and Y are hydroxyl groups can be selectively produced by reacting compound (IV) wherein X and Y are hydroxyl groups, with compound (V') in the absence of a base.

A cis form-trans form mixture or cis form of cysteine derivative (I) is obtained by reacting compound (IV) with compound (V) or compound (V') in the presence of an inorganic base. The ratio of cis form:trans form of the resultant product by these reaction varies depending on the ratio of cis form:trans form of compound (IV).

In the production method by the above-mentioned a), examples of the organic base include triethylamine, pyridine, N-methylmorpholine, diisopropylethylamine, and the like, and triethylamine is preferable. This reaction can be carried out in the presence or absence of a solvent. Examples of the solvent include ethyl acetate, isopropyl acetate, tetrahydrofuran, acetone, and the like, and ethyl acetate is preferable. The amount of compound (V) or compound (V') to be used is 1.0 to 5.0 mol, preferably 1.2 to 3.0 mol, per 1 mol of compound (IV). When a base is used, the amount of the base to be used is 1.0 to 5.0 mol, preferably 1.2 to 4.0 mol, per 1 mol of compound (IV). The reaction temperature is −10 to 100° C., preferably 0 to 90° C. The reaction time is 1 to 48 hours, preferably 3 to 20 hours.

The "selective" production of trans form or cis form means that the ratio of trans form or cis form of the whole of the obtained cysteine derivative (I) is generally 70% or more, preferably 85% or more, more preferably 90% or more.

As mentioned above, since cysteine derivative (I) is preferably a trans form from the aspects of stability, it is preferably synthesized by production method a). The trans form of cysteine derivative (I) synthesized by production method a) can be converted to the trans form of other cysteine derivative (I) (e.g., X, Y=OH) by hydrolysis and the like.

Production Method 4.

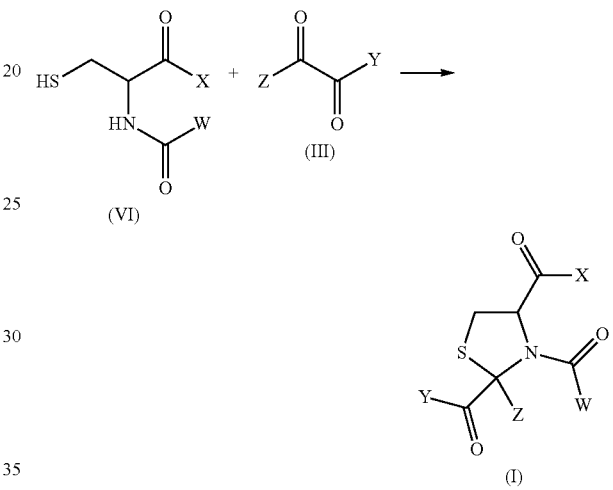

wherein each symbol is as defined above.

Cysteine derivative (I) can be synthesized by reacting compound (VI), which is N-acylated-, N-alkoxycarbonylated- or N-alkylcarbamoylated-cysteine derivative, with compound (III). Cysteine derivative (I) may be converted to other cysteine derivative (I) by esterification, amidation, hydrolysis or the like.

Cysteine derivative (IX) can be produced according to the above-mentioned production method of cysteine derivative (I).

Other features of the invention will become apparent in the course of the following descriptions of exemplary embodiments which are given for illustration of the invention and are not intended to be limiting thereof.

EXAMPLES

When plural isomers are contained as resultant products, the isomer to be the main resultant product was subjected to NMR measurement. The measurement was performed using Bruker AVANCE 400 manufactured by Bruker. The cis form and trans form was determined by an X ray crystal structure analysis of each crystal.

Reference Example 1

2-methylthiazolidine-2,4-dicarboxylic acid (cysteinylpyruvic acid; hereinafter sometimes to be abbreviated as CP in the present specification)

Under an argon atmosphere, L-cysteine (15 g) was dissolved in dry ethanol (35 mL), pyruvic acid (18.6 mL) was added thereto at room temperature, and the mixture was stirred for 3 hours. The resulting solid was collected by filtration under reduced pressure, and washed with ice-cooled ethanol to give 2-methylthiazolidine-2,4-dicarboxylic acid (diastereomer mixture) (23 g, yield 97%).

$^1$H-NMR (DMSO-$d_6$) δ; 1.59 (3H, s), 1.72 (3H, s), 2.76 (1H, dd), 2.97 (1H, dd), 3.26 (1H, dd), 3.40 (1H, dd), 3.98 (1H, dd), 4.19 (1H, dd); MS spectrum m/z; 190 (M).

Reference Example 2

2-methylthiazolidine-2,4-dicarboxylic acid 2-ethyl ester (hereinafter sometimes to be abbreviated as CP2Et in the present specification)

Under an argon atmosphere, L-cysteine (10 g) was dissolved in pure water (150 ml), and ethyl pyruvate (19.7 ml) dissolved in ethanol (10 ml) at room temperature was gradually added to the solution. The mixture was stirred overnight at room temperature, and concentrated under reduced pressure. The obtained solid was dissolved in pure water, and the solution was extracted with chloroform. The extract was dried over magnesium sulfate, and concentrated under reduced pressure to give an oil. The oil was recrystallized from chloroform/hexane to give 2-methylthiazolidine-2,4-dicarboxylic acid 2-ethyl ester (diastereomer mixture) (12.7 g, yield 70%).

$^1$H-NMR (DMSO-$d_6$) δ; 1.19 (3H, t), 1.23 (3.9H, t), 1.62 (3H, s), 1.75 (3H, s), 1.75 (3H, s), 2.81 (1.3H, t), 2.97 (1H, dd), 3.29 (1H, dd), 3.42 (1.3H, dd), 4.03 (1.3H, dd), 4.09 (2H, m), 4.16 (1H, dd), 4.20 (2.6H, q); MS spectrum m/z; 220 (M$^+$).

Synthetic Example 1

N-acetyl-2-methylthiazolidine-2,4-dicarboxylic acid 2-ethyl ester (hereinafter sometimes to be abbreviated as N-Ac-CP2Et in the present specification)

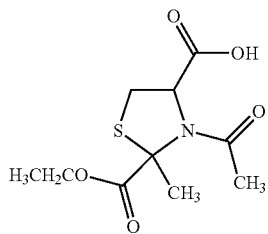

2-Methylthiazolidine-2,4-dicarboxylic acid 2-ethyl ester (10.0 g, 45.6 mmol) obtained by a method similar to that in Reference Example 2 was dissolved in THF (100 ml), and the solution was kept at 0° C. To the solution was added triethylamine (12.7 ml, 91.2 mmol), and acetyl chloride (6.5 ml, 91.2 mmol) was added dropwise thereto over 10 minutes. The reaction temperature was allowed to gradually rise, and the mixture was stirred overnight at room temperature. The reaction mixture was concentrated under reduced pressure. To the residue was added ethyl acetate, and the mixture was washed with water. The ethyl acetate layer was washed with 5% aqueous citric acid, 5% aqueous sodium hydrogen carbonate and saturated brine, dried over anhydrous magnesium sulfate, and concentrated under reduced pressure. The residue was purified by silica gel column chromatography (eluted with ethyl acetate-5% acetic acid) to give N-acetyl-2-methylthiazolidine-2,4-dicarboxylic acid 2-ethyl ester (trans form) as a pale-brown oil (7.7 g, 64.6%).

$^1$H-NMR (CDCl$_3$): δ; 1.27 (3H, t, J=7.12 Hz), 1.94 (3H, s), 2.18 (3H, s), 3.40 (1H, d, J=11.6 Hz), 3.56 (1H, dd, J=5.5, 11.0 Hz), 4.20 (2H, t, J=7.08 Hz), 5.00 (1H, d, J=5.9 Hz), 9.10 (1H, brs).

Synthetic Example 2

Crystal of N-acetyl-2-methylthiazolidine-2,4-dicarboxylic acid 2-ethyl ester

The crude product of N-acetyl-2-methylthiazolidine-2,4-dicarboxylic acid 2-ethyl ester (10.28 g, oil) obtained by a method similar to that in Synthetic Example 1 was purified by silica gel column chromatography (eluent: ethyl acetate: acetic acid=95:5, volume ratio), and the fraction was concentrated under reduced pressure. To the residue was added toluene, and the mixture was concentrated under reduced pressure to give an amorphous pale-yellow substance. The substance was recrystallized from ethyl acetate and n-hexane to give N-acetyl-2-methylthiazolidine-2,4-dicarboxylic acid 2-ethyl ester (trans form) as pale-yellow crystals (7.0 g, about 59%).

$^1$H-NMR (DMSO-$d_6$): δ; 1.15 (3H, t, J=7.08 Hz), 1.77 (3H, s), 2.03 (3H, s), 5.33 (1H, d, J=4.64 Hz).

Synthetic Example 3

N-acetyl-2-methylthiazolidine-2,4-dicarboxylic acid 2-ethyl ester

2-Methylthiazolidine-2,4-dicarboxylic acid 2-ethyl ester (2.00 g, 9.14 mmol) obtained by a method similar to that in Reference Example 2 was dissolved in ethyl acetate (20 ml), and the solution was kept at 0° C. To the solution was added pyridine (1.48 ml, 18.3 mmol), and acetyl chloride (0.97 ml, 13.7 mmol) was added dropwise thereto. The reaction temperature was allowed to gradually rise, and the mixture was stirred at room temperature for 4 hours. To the reaction mixture was added 5% aqueous citric acid, and the mixture was extracted with ethyl acetate. The extract was washed with water and saturated brine, dried over anhydrous magnesium sulfate, and concentrated under reduced pressure to give N-acetyl-2-methylthiazolidine-2,4-dicarboxylic acid 2-ethyl ester (with the ratio of trans form of about 75% as confirmed by NMR) as a pale-brown oil (2.02 g).

Synthetic Example 4

N-acetyl-2-methylthiazolidine-2,4-dicarboxylic acid 2-ethyl ester

By an operation similar to that in Synthetic Example 3 except for the use of N-methylmorpholine (2.01 ml, 18.3 mmol) instead of pyridine, N-acetyl-2-methylthiazolidine-2,4-dicarboxylic acid 2-ethyl ester (with the ratio of trans form of about 80% as confirmed by NMR) was obtained as a pale-brown oil (1.93 g).

Synthetic Example 5

N-acetyl-2-methylthiazolidine-2,4-dicarboxylic acid 2-ethyl ester

By an operation similar to that in Synthetic Example 3 except for the use of diisopropylethylamine instead of pyridine, N-acetyl-2-methylthiazolidine-2,4-dicarboxylic acid 2-ethyl ester (with the ratio of trans form of about 90% as confirmed by NMR) was obtained as a orange-yellow oil.

Synthetic Example 6

N-acetyl-2-methylthiazolidine-2,4-dicarboxylic acid 2-ethyl ester

By an operation similar to that in Synthetic Example 3 except that potassium carbonate (2.54 g, 18.4 mmol) was used instead of pyridine and the mixture was stirred for 16 hours instead of 4 hours, N-acetyl-2-methylthiazolidine-2,4-dicarboxylic acid 2-ethyl ester (with the ratio of cis form:trans form of about 47:53 as confirmed by NMR) was obtained as a colorless oil (0.895 g).

Synthetic Example 7

N-acetyl-2-methylthiazolidine-2,4-dicarboxylic acid 2-ethyl ester

By an operation similar to that in Synthetic Example 6 except for the use of 2N HCl instead of 5% aqueous citric acid, N-acetyl-2-methylthiazolidine-2,4-dicarboxylic acid 2-ethyl ester was obtained as a pale-yellow oil. To the oil was added n-hexane, and the mixture was concentrated under reduced pressure. To the residue was n-hexane to allow solidification of the residue. The solid was collected by filtration, and dried under reduced pressure to give a crystal of N-acetyl-2-methylthiazolidine-2,4-dicarboxylic acid 2-ethyl ester (with the ratio of cis form:trans form of about 50:50 as confirmed by NMR) was obtained (22.33 g).
$^1$H-NMR (CDCl$_3$, 400 MHz): δ:
trans: 1.29 (3H, t, J=7.11 Hz), 1.96 (3H, s), 2.19 (3H, s), 3.42 (1H, d, J=11.7 Hz), 3.60 (1H, dd, J=6.28, 11.8 Hz), 4.16-4.29 (2H, m), 5.03 (1H, d, J=5.97 Hz).
cis: 1.38 (3H, t, J=7.13 Hz), 1.95 (3H, s), 2.16 (3H, s), 3.47 (1H, dd, J=1.66, 12.2 Hz), 3.72 (1H, dd, J=6.79, 12.2 Hz), 4.33-4.48 (2H, m), 4.98 (1H, dd, J=1.68, 6.78 Hz).

Synthetic Example 8

N-acetyl-2-methylthiazolidine-2,4-dicarboxylic acid 2-ethyl ester

By a method similar to that in Synthetic Example 7 except for the use of 2-methylthiazolidine-2,4-dicarboxylic acid 2-ethyl ester synthesized from D-cysteine by a method similar to that in Reference Example 2, N-acetyl-2-methylthiazolidine-2,4-dicarboxylic acid 2-ethyl ester was obtained (with the ratio of cis form:trans form of about 43:57 as confirmed by NMR).

Synthetic Example 9

N-acetyl-2-methylthiazolidine-2,4-dicarboxylic acid 2-ethyl ester

2-Methylthiazolidine-2,4-dicarboxylic acid 2-ethyl ester (1.00 g, 4.59 mmol) obtained by a method similar to that in Reference Example 2 was dissolved in ethyl acetate (10 ml), and the solution was kept at 0° C. To the solution was added dropwise acetic anhydride (1.29 ml, 13.7 mmol), and the reaction mixture was heated under reflux for 3 hours. The reaction mixture was concentrated under reduced pressure, toluene was added thereto, and the mixture was concentrated under reduced pressure. To the residue was added ethyl acetate, and the mixture was washed with water and saturated brine, dried over anhydrous magnesium sulfate, and concentrated under reduced pressure. To the residue was added water, and the mixture was stirred. Water was removed by decantation, and the residue was concentrated under reduced pressure. To the residue were added ethyl acetate and n-hexane to allow solidification of the residue. The solid was collected by filtration, and dried under reduced pressure to give N-acetyl-2-methylthiazolidine-2,4-dicarboxylic acid 2-ethyl ester (trans form) (0.56 g).

Synthetic Example 10

N-acetyl-2-methylthiazolidine-2,4-dicarboxylic acid 2-ethyl ester

L-Cysteine hydrochloride monohydrate (100 g, 569 mmol) was dissolved in water (200 ml), and the pH of the solution was adjusted to 5.07 with 6N aqueous sodium hydroxide. The reaction mixture was heated to 40° C., ethyl pyruvate (76 ml, 684 mmol) was gradually added thereto, and the mixture was stirred at 40° C. for 3.5 hours to give 2-methylthiazolidine-2,4-dicarboxylic acid 2-ethyl ester (the ratio of trans form:cis form of the resultant product in the reaction mixture was confirmed by the area ratio of an HPLC chart to find about 55:45). After completion of the reaction, the reaction mixture was extracted with ethyl acetate. The extract was washed with saturated brine, and dried over anhydrous magnesium sulfate. To the obtained ethyl acetate solution was added triethylamine (159 ml, 1141 mmol) under argon, and acetyl chloride (61 ml, 858 mmol) was slowly added dropwise thereto. The reaction mixture was heated under reflux for 4 hr to give N-acetyl-2-methylthiazolidine-2,4-dicarboxylic acid 2-ethyl ester (the ratio of trans form:cis form of the resultant product in the reaction mixture was confirmed by the area ratio of an HPLC chart to find about 95:5). After completion of the reaction, water (100 ml) was added thereto, and the pH of the mixture was adjusted to 2.5 with HCl. The aqueous layer was separated, and extracted with ethyl acetate. The extract was washed with saturated brine, and dried over anhydrous magnesium sulfate. The obtained ethyl acetate solution was concentrated until a weight of 900 g, to the residue was added heptane to allow recrystallization of the residue, and the crystals were washed with heptane/ethyl acetate=2/1, and dried at 50° C. under reduced pressure to give a crystal of a trans form of N-acetyl-2-methylthiazolidine-2,4-dicarboxylic acid 2-ethyl ester (the ratio of trans form:cis form of the resultant product in the reaction mixture was confirmed by the area ratio of an HPLC chart to find about 99%) (84 g, yield 57%). The melting point of the obtained crystal was measured using digital melting point measuring apparatus IA9100 manufactured by Electrothermal to be 138° C. to 141° C.

Synthetic Example 11

N-acetyl-2-methylthiazolidine-2,4-dicarboxylic acid 2-ethyl ester

D-Cysteine hydrochloride monohydrate (10 g, 57 mmol) was dissolved in water (20 ml), and the pH of the solution was adjusted to 5.13 with 6N aqueous sodium hydroxide solution. The reaction mixture was heated to 40° C., ethyl pyruvate (7.6 ml, 68 mmol) was gradually added thereto, and the mixture was stirred at 40° C. for 4.5 hours to give 2-methylthiazolidine-2,4-dicarboxylic acid 2-ethyl ester (the ratio of trans form:cis form of the resultant product in the reaction mixture was confirmed by NMR to find about 55:45). After completion of the reaction, the reaction mixture was extracted with ethyl acetate. The extract was washed with saturated brine, and dried over magnesium sulfate. To the obtained ethyl acetate solution was added triethylamine (16 ml, 115 mmol) under argon, acetyl chloride (6.1 ml, 86 mmol) was slowly added dropwise thereto, and the reaction mixture was heated under reflux for 3 hr to give N-acetyl-2-methylthiazolidine-2,4-dicarboxylic acid 2-ethyl ester (the ratio of trans form:cis form of the resultant product in the reaction mixture was confirmed by NMR to be about 97:3). After completion of the reaction, water (30 ml) was added thereto, and the pH of the mixture was adjusted to 0.9 with 5.7M HCl. The aqueous layer was separated, and extracted with ethyl acetate. The extract was washed with saturated brine, and dried over anhydrous magnesium sulfate. The obtained ethyl acetate solution was concentrated to a weight of 157 g, and to the residue was heptane to be recrystallize the residue. The solid was washed with heptane/ethyl acetate=1.5/1, and dried at 50° C. under reduced pressure to give a crystal of a trans form of N-acetyl-2-methylthiazolidine-2,4-dicarboxylic acid 2-ethyl ester (the ratio of the trans form was confirmed by the area ratio of an HPLC chart to find about 99%) (10.7 g, yield 71%).

HPLC analysis conditions in Synthetic Examples 10 and 11 and the following Synthetic Example 41
detector: ultraviolet absorption spectrophotometer (measurement wavelength; 210 nm)
column: YMC-Pack ODS-A (particle size 5 μm, fine pore size 12 mm, inner diameter 6.0 mm, length 150 mm)
eluent: 50 mM $NaH_2PO_4$ (adjusted to pH 2 with 85% $H_3PO_4$): MeOH=60:40
flow rate: 1.0 mL/minute
column temperature: 40° C.
injection volume: 10 μL
retention time (min): CP2Et (cis form): 9.0, CP2Et (trans form): 8.6, N-Ac-CP2Et (cis form): 7.5, (trans form): 9.2

Synthetic Example 12

N-acetyl-2-methylthiazolidine-2,4-dicarboxylic acid 2-ethyl ester Na salt

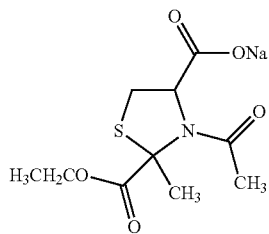

The crude product (2.01 g, oil) of N-acetyl-2-methylthiazolidine-2,4-dicarboxylic acid 2-ethyl ester, which was obtained by a method similar to that in Synthetic Example 1, was dissolved in ethanol (15 ml), and 4N NaOH (1.54 ml, about 6.2 mmol) was added thereto. The mixture was stirred at room temperature for 2.5 hours, and concentrated under reduced pressure to give an amorphous substance. This was dried under reduced pressure to give N-acetyl-2-methylthiazolidine-2,4-dicarboxylic acid 2-ethyl ester Na salt (trans form) as a pale-yellow powder (1.95 g, about 89%).

$^1$H-NMR ($D_2O$): δ; 1.17 (3H, t), 1.78 (3H, s), 2.05 (3H, s), 3.32 (1H, d, J=11.8 Hz), 4.12 (2H, t), 4.93 (1H, d, J=5.68 Hz).

Synthetic Example 13

N-acetyl-2-methylthiazolidine-2,4-dicarboxylic acid (N-acetyl-cysteinylpyruvic acid; hereinafter sometimes to be abbreviated as N-Ac-CP)

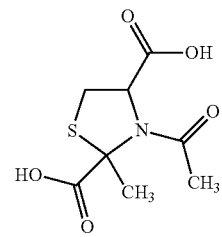

N-Acetyl-2-methylthiazolidine-2,4-dicarboxylic acid 2-ethyl ester obtained by an operation similar to that in Synthetic Example 1 was dissolved in a mixed solvent of methanol (120 ml) and water (120 ml), and 2N NaOH (182.4 ml) was added thereto. The reaction mixture was heated with stirring under an argon atmosphere at 100° C. for 4 hours, and then at 80° C. overnight. The reaction mixture was allowed to cool to room temperature, and the pH was adjusted to 1 to 2 with AMBERLITE IR120B H AG (about 250 g). The AMBERLITE was removed by filtration, and the filtrate was concentrated under reduced pressure. To the residue was ethyl acetate (200 ml), the mixture was stirred for 1 hour, and the resulting white crystals were collected by filtration to give N-acetyl-2-methylthiazolidine-2,4-dicarboxylic acid (trans form) (15.99 g, 75%).

$^1$H-NMR (DMSO-$d_6$): δ; 1.73 (3H, s), 2.01 (3H, s), 3.36 (2H, d, J=3.6 Hz), 5.26 (1H, t, J=3.6 Hz); MS spectrum m/z; [M+H]$^+$=234.0, [M−H]$^-$=232.0.

Synthetic Example 14

N-acetyl-2-methylthiazolidine-2,4-dicarboxylic acid 2Na salt

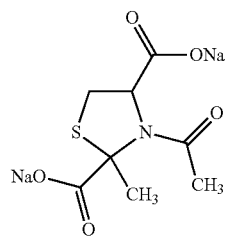

The crude product (10.19 g) of N-acetyl-2-methylthiazolidine-2,4-dicarboxylic acid 2-ethyl ester, which was obtained by a method similar to that in Synthetic Example 13, was dissolved in ethanol (20 ml), and 4N NaOH was added thereto. The mixture was stirred under an argon atmosphere, and ethanol was added thereto to give a pale-yellow solid. The obtained solid was collected by filtration to give N-acetyl-2-methylthiazolidine-2,4-dicarboxylic acid 2Na salt (trans form) as crystals (9.09 g, about 72%).

$^1$H-NMR (D$_2$O): δ; 1.73 (3H, s), 2.01 (3H, s), 3.15 (1H, d, J=11.4 Hz), 3.39 (1H, dd, J=6.6, 11.7 Hz), 4.80 (1H, d, J=6.5 Hz).

Synthetic Example 15

N-acetyl-2-methylthiazolidine-2,4-dicarboxylic acid

By an operation similar to that in Synthetic Example 13 and using 2-methylthiazolidine-2,4-dicarboxylic acid 2-ethyl ester synthesized from DL-cysteine by a method similar to that in Reference Example 2, N-acetyl-2-methylthiazolidine-2,4-dicarboxylic acid (trans form) was obtained as a white solid (yield 70%).

Synthetic Example 16

N-acetyl-2-methylthiazolidine-2,4-dicarboxylic acid

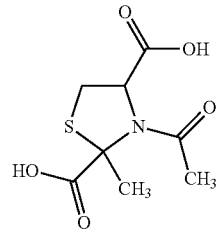

2-Methylthiazolidine-2,4-dicarboxylic acid (20 g, 104.6 mmol) obtained by a method similar to that in Reference Example 1 and acetic anhydride (40 ml, 418.3 mmol) were heated at 100° C. for 2 hours. The reaction mixture was concentrated under reduced pressure, 5% aqueous citric acid (200 ml) was added thereto, and the mixture was stirred overnight at room temperature. Concentrated hydrochloric acid (2 ml) was added thereto, and the mixture was stirred at 70° C. for 1 hour. The reaction mixture was filtered off to remove tar substance, and the filtrate was concentrated under reduced pressure to a volume of about 100 ml. The mixture was extracted with ethyl acetate. The extract was washed with saturated brine, dried over anhydrous magnesium sulfate, and concentrated under reduced pressure to give N-acetyl-2-methylthiazolidine-2,4-dicarboxylic acid (16.3 g) as an amorphous substance. To the amorphous substance was added water to allow recrystallization of the substance, and the obtained crystals were dried under reduced pressure to give N-acetyl-2-methylthiazolidine-2,4-dicarboxylic acid (cis form) as a white solid (5.3 g, 23%).

$^1$H-NMR (DMSO-d$_6$): δ; 1.80 (3H, s), 2.02 (3H, s), 3.49 (1H, dd, J=1.04, 12.00 Hz), 3.61 (1H, dd, J=6.30, 12.00 Hz), 5.22 (1H, dd, J=6.24, 1.04); MS spectrum m/z; [M+H]$^+$=234.0, [M−H]$^-$=232.0.

Synthetic Example 17

N-acetyl-2-methylthiazolidine-2,4-dicarboxylic acid

By an operation similar to that in Synthetic Example 16 and using 2-methylthiazolidine-2,4-dicarboxylic acid synthesized from DL-cysteine by a method similar to that in Reference Example 1, N-acetyl-2-methylthiazolidine-2,4-dicarboxylic acid (cis form) was obtained as an amorphous substance (yield 44%).

Synthetic Example 18

N-acetyl-2-methylthiazolidine-2,4-dicarboxylic acid anhydride

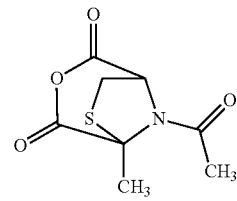

2-Methylthiazolidine-2,4-dicarboxylic acid (2.0 g, 10.5 mmol) obtained by a method similar to that in Reference Example 1 and acetic anhydride (4.0 ml, 42.0 mmol) were heated at 100° C. for 2 hours. The reaction mixture was concentrated under reduced pressure, and the residue was extracted with ethyl acetate. The extract was washed with saturated brine, dried over anhydrous magnesium sulfate, and concentrated under reduced pressure to give N-acetyl-2-methylthiazolidine-2,4-dicarboxylic acid anhydride (2.12 g) as an amorphous substance. The amorphous substance was purified by silica gel chromatography (eluted with n-hexane-ethyl acetate) to give N-acetyl-2-methylthiazolidine-2,4-dicarboxylic acid anhydride (cis form) as a white solid (1.2 g, 53%).

$^1$H-NMR (DMSO-d$_6$): δ; 1.78 (3H, s), 1.89 (3H, s), 3.63 (1H, dd, J=0.84, 12.64 Hz), 3.86 (1H, dd, J=5.76, 12.64 Hz), 4.91 (1H, dd, J=0.92, 5.72).

Synthetic Example 19

N-acetyl-2-methylthiazolidine-2,4-dicarboxylic acid 2,4-diethyl ester

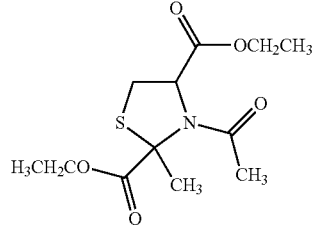

N-Acetyl-2-methylthiazolidine-2,4-dicarboxylic acid 2-ethyl ester (1.5 g, 5.74 mmol) obtained by a method similar to that in Synthetic Example 1 was dissolved in dichloromethane (30 ml), and the reaction mixture was kept at 0° C. To the solution were added ethanol (0.40 ml, 6.89 mmol), EDCI HCl (1.32 g, 6.89 mmol) and DMAP (4-dimethylaminopyridine, 0.14 g, 1.15 mmol). The reaction temperature was allowed to gradually rise from 0° C., and the mixture was stirred overnight at room temperature. The reaction mixture was concentrated under reduced pressure, to the residue was added ethyl acetate, and the mixture was washed with water. The ethyl acetate layer was washed with 5% aqueous citric acid, 5% aqueous sodium hydrogen carbonate and saturated brine, dried over anhydrous magnesium sulfate, and concentrated under reduced pressure to give N-acetyl-2-methylthiazolidine-2,4-dicarboxylic acid 2,4-diethyl ester (trans form) as a pale-brown oil (0.69 g, 41.3%).

$^1$H-NMR (CDCl$_3$): δ; 1.27 (3H, t, J=7.12 Hz), 1.33 (3H, t, J=7.16 Hz), 1.93 (3H, s), 2.12 (3H, s), 3.36 (1H, dd, J=0.52, 11.68 Hz), 3.54 (1H, dd, J=6.16, 11.64 Hz), 4.12-4.25 (2H, m), 4.25-4.33 (2H, m), 4.95 (1H, d, J=5.84 Hz).

Synthetic Example 20

N-acetyl-2-methylthiazolidine-2,4-dicarboxylic acid 2-ethyl 4-isopropyl ester

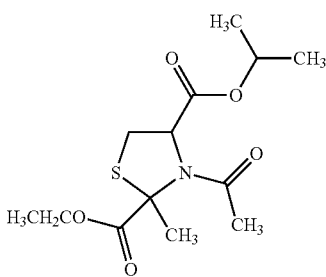

N-Acetyl-2-methylthiazolidine-2,4-dicarboxylic acid 2-ethyl ester (1.5 g, 5.74 mmol) obtained by a method similar to that in Synthetic Example 1 was dissolved in dichloromethane (30 ml), and the reaction mixture was kept at 0° C. To the solution were added isopropanol (0.53 ml, 6.89 mmol), EDCI HCl (1-ethyl-3-(3-dimethylaminopropyl)-carbodiimide hydrochloride, 1.32 g, 6.89 mmol), and DMAP (0.14 g, 1.15 mmol). The reaction temperature was allowed to gradually rise from 0° C., and the mixture was stirred overnight at room temperature. The reaction mixture was concentrated under reduced pressure, to the residue was added ethyl acetate, and the mixture was washed with water. The ethyl acetate layer was washed with 5% aqueous citric acid, 5% aqueous sodium hydrogen carbonate and saturated brine, dried over anhydrous magnesium sulfate, and concentrated under reduced pressure to give N-acetyl-2-methylthiazolidine-2,4-dicarboxylic acid 2-ethyl 4-isopropyl ester (trans form) as a pale-brown oil (0.68 g, 39.0%).

$^1$H-NMR (CDCl$_3$): δ; 1.12-1.17 (9H, m), 1.93 (3H, s), 1.96 (3H, s), 3.35 (1H, d, J=11.4 Hz), 3.53 (1H, dd, J=6.3, 11.4 Hz), 4.14-4.29 (2H, m), 4.90 (1H, d, J=6.0 Hz), 5.14 (1H, q, J=6.0 Hz).

Synthetic Example 21

N-tert-butoxycarbonyl-2-methylthiazolidine-2,4-dicarboxylic acid 2-ethyl ester

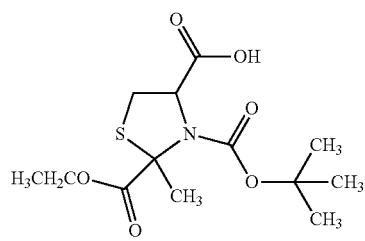

2-Methylthiazolidine-2,4-dicarboxylic acid 2-ethyl ester (1.1 g, 5.02 mmol) obtained by a method similar to that in Reference Example 2 was dissolved in THF (10 ml), and the reaction mixture was kept at 0° C. To the solution were added (Boc)$_2$O (di-t-butyl dicarbonate, 1.3 g, 6.02 mmol), and triethylamine (0.77 ml, 5.52 mmol). The reaction temperature was allowed to gradually rise from 0° C., and the mixture was stirred overnight at room temperature. To the reaction mixture was added DMAP (0.30 g, 2.50 mmol), and the mixture was stirred at room temperature for additional 6 hours. The reaction mixture was concentrated under reduced pressure, to the residue was added ethyl acetate, and the mixture was washed with water. The ethyl acetate layer was washed with 5% aqueous citric acid, 5% aqueous sodium hydrogen carbonate and saturated brine, dried over anhydrous magnesium sulfate, and concentrated under reduced pressure to give N-tert-butoxycarbonyl-2-methylthiazolidine-2,4-dicarboxylic acid 2-ethyl ester (with the ratio of cis form:trans form of about 50:50 as confirmed by NMR) as a pale-yellow oil (1.00 g, 62.4%).

$^1$H-NMR (CDCl$_3$): δ; 1.24-1.32 (9H, m), 1.97 (1.5H, d, J=6.84 Hz), 2.05 (1.5H, s), 3.26-3.52 (2H, m), 4.15-4.30 (2H, m), 4.78-4.90 (1H, m).

Synthetic Example 22

N-acetyl-2-methylthiazolidine-2,4-dicarboxylic acid 2-ethyl ester 4-glycine ethyl ester amide

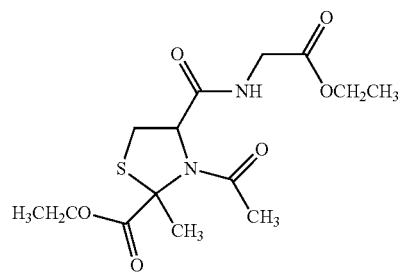

N-Acetyl-2-methylthiazolidine-2,4-dicarboxylic acid 2-ethyl ester (0.200 g, 0.77 mmol) obtained by a method similar to that in Synthetic Example 1 was dissolved in dichloromethane (2 ml), and the reaction mixture was kept at 0° C. To the solution were added glycine ethyl ester hydrochloride (0.107 g, 0.77 mmol), triethylamine (0.120 ml, 0.87 mmol), HOBt H$_2$O (1-hydroxybenzotriazole hydrate, 0.113 g, 0.84 mmol), and EDCI HCl (0.161 g, 0.84 mmol). The reaction temperature was allowed to gradually rise from 0° C., and the mixture was stirred overnight at room temperature. The reaction mixture was concentrated under reduced pressure, to the residue was added ethyl acetate, and the mixture was washed with water. The ethyl acetate layer was washed with 5% aqueous citric acid, 5% aqueous sodium hydrogen carbonate and saturated brine, dried over anhydrous magnesium sulfate, and concentrated under reduced pressure to give N-acetyl-2-methylthiazolidine-2,4-dicarboxylic acid 2-ethyl ester 4-glycine ethyl ester amide (trans form) as a white solid (0.211 g, 80.0%).

$^1$H-NMR (CDCl$_3$): δ; 1.22-1.32 (6H, m), 2.05 (3H, s), 2.19 (3H, s), 3.35 (1H, d, J=11.84 Hz), 3.60 (1H, dd, J=6.96, 11.88 Hz), 4.12 (2H, t, J=5.08 Hz), 4.15-4.26 (4H, m), 4.88 (1H, d, J=6.8 Hz), 6.85 (1H, brs).

Synthetic Example 23

N-decanoyl-2-methylthiazolidine-2,4-dicarboxylic acid 2-ethyl ester

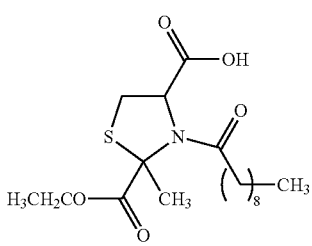

2-Methylthiazolidine-2,4-dicarboxylic acid 2-ethyl ester obtained by a method similar to that in Reference Example 2 was subjected to acylation with decanoyl chloride in the presence of triethylamine, and the mixture was purified by silica gel chromatography to give N-decanoyl-2-methylthiazolidine-2,4-dicarboxylic acid 2-ethyl ester (trans form) as white crystals (91.9%).

$^1$H-NMR (CDCl$_3$, 400 MHz): δ; 0.89 (3H, t, J=6.86 Hz), 1.28 (3H, t, J=7.10 Hz), 1.19-1.33 (12H, m), 1.61-1.68 (2H, m), 1.95 (3H, s), 2.30-2.34 (2H, m), 3.41 (1H, d, J=11.7 Hz), 3.58 (1H, dd, J=6.26, 11.7 Hz), 4.18-4.24 (2H, m), 5.06 (1H, d, J=5.98 Hz).

Synthetic Example 24

N-decanoyl-2-methylthiazolidine-2,4-dicarboxylic acid

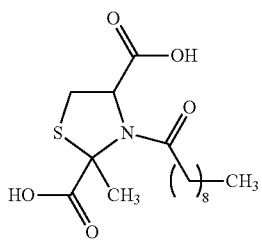

N-Decanoyl-2-methylthiazolidine-2,4-dicarboxylic acid 2-ethyl ester obtained by a method similar to that in Synthetic Example 23 was subjected to hydrolysis with sodium hydroxide (water-ethanol solvent) to give N-decanoyl-2-methylthiazolidine-2,4-dicarboxylic acid (trans form) as white crystals (55.0%).

$^1$H-NMR (CDCl$_3$, 400 MHz): δ; 0.90 (3H, t, J=6.87 Hz), 1.24-1.40 (12H, m), 1.62-1.73 (2H, m), 1.96 (3H, s), 2.27-2.40 (2H, m), 3.44 (1H, d, J=11.4 Hz), 3.62 (1H, bdd, J=6.23, 11.9 Hz), 5.06 (1H, d, J=6.57 Hz).

Synthetic Example 25

N-decanoyl-2-methylthiazolidine-2,4-dicarboxylic acid 2,4-diethyl ester

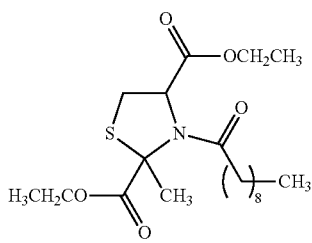

N-Decanoyl-2-methylthiazolidine-2,4-dicarboxylic acid 2-ethyl ester obtained by a method similar to that in Synthetic Example 23 was subjected to ethyl-esterification with ethanol, EDCI HCl and DMAP (dichloromethane solvent) to give N-decanoyl-2-methylthiazolidine-2,4-dicarboxylic acid 2,4-diethyl ester (trans form) as a yellow oil (75.3%).

$^1$H-NMR (CDCl$_3$, 400 MHz): δ; 0.89 (3H, t, J=6.89 Hz), 1.27 (3H, t, J=7.12 Hz), 1.34 (3H, t, J=7.13 Hz), 1.26-1.36 (12H, m), 1.61-1.66 (2H, m), 1.94 (3H, s), 2.22-2.31 (2H, m), 3.36 (1H, dd, J=0.53, 11.6 Hz), 3.51 (1H, dd, J=6.20, 11.6 Hz), 4.17-4.24 (2H, m), 4.27-4.33 (2H, m), 4.99 (1H, d, J=5.82 Hz).

Synthetic Example 26

N-hexadecanoyl-2-methylthiazolidine-2,4-dicarboxylic acid 2-ethyl ester

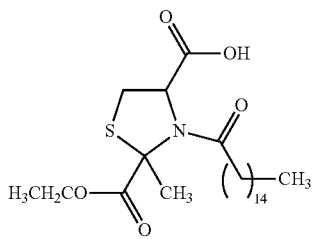

2-Methylthiazolidine-2,4-dicarboxylic acid 2-ethyl ester obtained by a method similar to that in Reference Example was subjected to acylation with hexadecanoyl chloride in the presence of triethylamine, and the mixture was purified by silica gel column chromatography to give N-hexadecanoyl-2-methylthiazolidine-2,4-dicarboxylic acid 2-ethyl ester (trans form) as white crystals (63.2%).

$^1$H-NMR (CDCl$_3$, 400 MH): δ; 0.90 (3H, t, J=6.86 Hz), 1.28 (3H, t, J=7.10 Hz), 1.27-1.36 (27 Hz, m), 1.62-1.67 (2H, m), 1.96 (3H, s), 2.27-2.33 (2H, m), 3.40 (1H, d, J=11.6 Hz), 3.59 (1H, dd, J=6.27, 11.8 Hz), 4.18-4.28 (2H, m), 5.60 (1H, d, J=5.98 Hz).

Synthetic Example 27

N-hexadecanoyl-2-methylthiazolidine-2,4-dicarboxylic acid

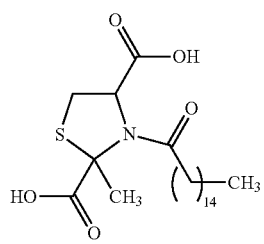

N-Hexadecanoyl-2-methylthiazolidine-2,4-dicarboxylic acid 2-ethyl ester obtained by a method similar to that in Synthetic Example 26 was subjected to hydrolysis with sodium hydroxide (water-ethanol solvent) to give N-hexadecanoyl-2-methylthiazolidine-2,4-dicarboxylic acid (trans form) as a white solid (86.8%).

$^1$H-NMR (CDCl$_3$, 400 MHz): δ; 0.88 (3H, t, J=6.86 Hz), 1.23-1.29 (24H, m), 1.62-1.67 (2H, m), 1.94 (3H, s), 2.25-2.36 (2H, m), 3.42 (1H, d, J=11.2 Hz), 3.59 (1H, bdd, J=6.12, 11.9 Hz), 5.04 (1H, d, J=6.66 Hz).

Synthetic Example 28

N-hexadecanoyl-2-methylthiazolidine-2,4-dicarboxylic acid 2,4-diethyl ester

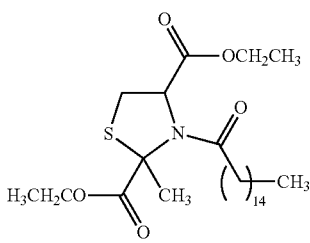

N-Hexadecanoyl-2-methylthiazolidine-2,4-dicarboxylic acid 2-ethyl ester obtained by a method similar to that in Synthetic Example 26 was subjected to ethyl-esterification with ethanol, EDCI HCl and DMAP (dichloromethane solvent) to give N-hexadecanoyl-2-methylthiazolidine-2,4-dicarboxylic acid 2,4-diethyl ester (trans form) as a colorless oil (1000).

$^1$H-NMR (CDCl$_3$, 400 MHz): δ; 0.88 (3H, t, J=6.86 Hz), 1.26 (3H, t, J=7.07 Hz), 1.32 (3H, t, J=7.13 Hz), 1.21-1.34 (24H, m), 1.59-1.65 (2H, m), 1.93 (3H, s), 2.22-2.30 (2H, m), 3.35 (1H, dd, J=0.45, 11.6 Hz), 3.53 (1H, dd, J=6.19, 11.6 Hz), 4.16-4.22 (2H, m), 4.26-4.32 (2H, m), 4.97 (1H, d, J=5.82 Hz).

Synthetic Example 29

N-acetyl-2-methylthiazolidine-2,4-dicarboxylic acid 2-methyl ester

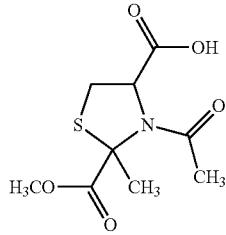 [SMILES: COC(=O)C1(C)SCC(C(=O)O)N1C(C)=O]

In the same manner as in Reference Example 2, L-2-methylthiazolidine-2,4-dicarboxylic acid 2-methyl ester was synthesized from L-cysteine and pyruvic acid methyl ester, and the compound was subjected to acetylation with acetyl chloride in the presence of potassium carbonate to give N-acetyl-2-methylthiazolidine-2,4-dicarboxylic acid 2-methyl ester (with the ratio of cis form:trans form of about 44:56 as confirmed by NMR) as a white solid (80.2%).

$^1$H-NMR (DMSO-d$_6$, 400 MHz): δ; trans: 1.75 (3H, s), 2.03 (3H, s), 3.35 (1H, dd, J=5.85, 11.7 Hz), 3.41 (1H, dd, J=1.04, 11.6 Hz), 3.61 (3H, s), 5.35 (1H, dd, J=0.956, 5.74 Hz).

$^1$H-NMR (CDCl$_3$, 400 MHz) δ: trans: 1.95 (3H, s), 2.19 (3H, s), 3.49 (1H, d, J=11.6 Hz), 3.58 (1H, dd, J=6.74, 12.2 Hz), 3.76 (3H, s), 5.01 (1H, d, J=5.80 Hz). cis: 2.01 (3H, s), 2.17 (3H, s), 3.49 (1H, dd, J=1.68, 12.3 Hz), 3.72 (1H, dd, J=6.74, 12.2 Hz), 3.95 (3H, s), 5.00 (1H, dd, J=1.68, 6.64 Hz).

Synthetic Example 30

N-acetyl-2-methylthiazolidine-2,4-dicarboxylic acid 2-ethyl 4-methyl ester

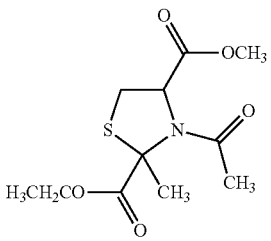

N-Acetyl-2-methylthiazolidine-2,4-dicarboxylic acid 2-ethyl ester obtained by a method similar to that in Synthetic Example 7 was subjected to methyl-esterification with methanol, EDCI HCl and DMAP to give N-acetyl-2-methylthiazolidine-2,4-dicarboxylic acid 2-ethyl 4-methyl ester (with the ratio of cis form:trans form of about 40:60 as confirmed by NMR) as a colorless oil (88.6%).

$^1$H-NMR (CDCl$_3$, 400 MHz): δ; trans: 1.28 (3H, t, J=7.12 Hz), 1.94 (3H, s), 2.13 (3H, s), 3.37 (1H, dd, J=0.558, 11.7 Hz), 3.57 (1H, dd, J=6.19, 11.7 Hz), 4.17-4.26 (2H, m), 4.97 (1H, d, J=5.93 Hz). cis: 1.28 (3H, t, J=7.12 Hz), 1.96 (3H, s), 2.17 (3H, s), 3.50 (1H, dd, J=6.03, 11.8 Hz), 3.62 (1H, dd, J=1.78, 11.8 Hz), 3.85 (3H, s), 4.17-4.26 (2H, m), 4.88 (1H, dd, J=1.77, 6.00 Hz).

Synthetic Example 31

N-acetyl-2-methylthiazolidine-2,4-dicarboxylic acid 2-ethyl ester 4-glycine methyl ester amide

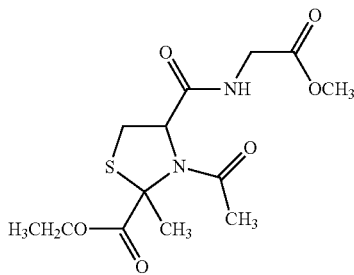

N-Acetyl-2-methylthiazolidine-2,4-dicarboxylic acid 2-ethyl ester obtained by a method similar to that in Synthetic Example 7 and glycine methyl ester hydrochloride were subjected to condensation with EDCI HCl, HOBt.H₂O, and triethylamine to give N-acetyl-2-methylthiazolidine-2,4-dicarboxylic acid 2-ethyl ester 4-glycine methyl ester amide (with the ratio of cis form:trans form of about 52:48 as confirmed by NMR) as a pale-yellow oil (93.7%).

¹H-NMR (CDCl₃, 400 MHz): δ; trans: 1.36 (3H, t, J=7.14 Hz), 1.99 (3H, s), 2.23 (3H, s), 3.44 (1H, dd, J=1.09, 12.3 Hz), 3.70 (1H, dd, J=7.03, 12.3 Hz), 3.76 (3H, s), 4.14-4.35 (4H, m), 4.84 (1H, dd, J=1.02, 7.00 Hz), 9.09 (1H, bs). cis: 1.30 (3H, t, J=7.12 Hz), 2.07 (3H, s), 2.21 (3H, s), 3.36 (1H, d, J=11.9 Hz), 3.62 (1H, dd, J=6.97, 11.9 Hz), 3.81 (3H, s), 4.14-4.35 (4H, m), 4.90 (1H, d, J=6.76 Hz), 6.89 (1H, bs).

Synthetic Example 32

N-acetyl-2-methylthiazolidine-2,4-dicarboxylic acid 2-ethyl ester 4-alanine methyl ester amide

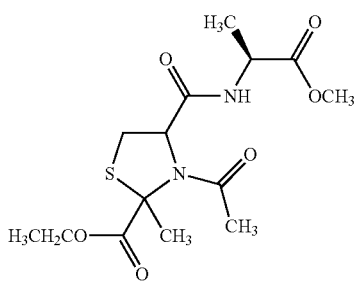

N-Acetyl-2-methylthiazolidine-2,4-dicarboxylic acid 2-ethyl ester obtained by a method similar to that in Synthetic Example 7 and L-alanine methyl ester hydrochloride were subjected to condensation with EDCI HCl, HOBt.H₂O, and triethylamine to give N-acetyl-2-methylthiazolidine-2,4-dicarboxylic acid 2-ethyl ester 4-glycine methyl ester amide (with the ratio of cis form:trans form of about 49:51 as confirmed by NMR) as a pale-yellow oil (1000).

¹H-NMR (CDCl₃, 400 MHz): δ; trans: 1.35 (3H, t, J=7.13 Hz), 1.48 (3H, d, J=7.20 Hz), 1.99 (3H, s), 2.24 (3H, s), 3.41 (1H, dd, J=0.88, 12.2 Hz), 3.67 (1H, dd, J=6.95, 12.2 Hz), 3.74 (3H, s), 4.19-4.24 (2H, m), 4.52-4.60 (1H, m), 4.80 (1H, dd, J=0.81, 6.89 Hz), 9.00 (1H, bs). cis: 1.29 (3H, t, J=7.12 Hz), 1.48 (3H, d, J=7.36), 2.02 (3H, s), 2.21 (3H, s), 3.35 (1H, d, J=11.9 Hz), 3.60 (1H, dd, J=6.93, 11.9 Hz), 3.78 (3H, s), 4.30-4.36 (2H, m), 4.62-4.68 (1H, m), 4.85 (1H, d, J=6.64 Hz), 6.83 (1H, bs).

Synthetic Example 33

N-acetylthiazolidine-2,4-dicarboxylic acid 2-ethyl ester

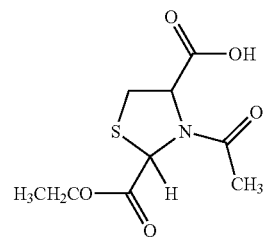

L-Cysteine (60.4 g, 0.50 mmol) and ethyl glyoxylate (polymer, 47% toluene solution, 50.9 g, 0.234 mol) were added to water (150 ml), and the mixture was stirred at room temperature for 50 hours. The obtained solution was concentrated under reduced pressure, and the precipitated solid was collected by filtration. The obtained white solid (about 40 g) was suspended in water (100 ml), and the suspension was stirred for 16 hours at slurry state. The white crystals were collected by filtration, and dried under reduced pressure to give thiazolidine-2,4-dicarboxylic acid 2-ethyl ester as a white solid (30.08 g).

Thiazolidine-2,4-dicarboxylic acid 2-ethyl ester (1.0 g, 4.89 mmol) was subjected to acylation with acetyl chloride (0.52 ml, 7.31 mmol) in the presence of triethylamine (1.02 ml, 7.33 mmol) to give N-acetylthiazolidine-2,4-dicarboxylic acid 2-ethyl ester (with the ratio of two kinds of stereoisomers of about 37:63 as confirmed by NMR) as an amorphous solid (1.19 g).

¹H-NMR (CDCl₃, 400 MHz): δ; isomer A: 1.29 (3H, t, J=7.10 Hz), 1.33 (3H, t, J=6.88 Hz), 2.18 (3H, s), 3.44 (1H, d, J=11.7 Hz), 3.68 (1H, dd, J=6.51, 12.0 Hz), 4.19-4.25 (2H, m), 4.94 (1H, d, J=6.09 Hz), 5.36 (1H, s). isomer B: 2.10 (3H, s), 3.33 (1H, dd, J=0.412, 12.2 Hz), 3.57 (1H, dd, J=7.18, 12.3 Hz), 4.19-4.32 (2H, m), 5.18 (1H, d, J=6.80 Hz), 5.27 (1H, s).

Synthetic Example 34

N-decanoylthiazolidine-2,4-dicarboxylic acid 2-ethyl ester

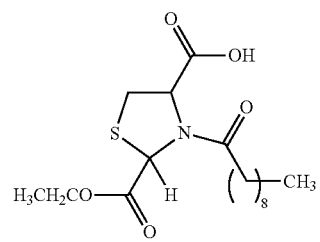

N-Acetylthiazolidine-2,4-dicarboxylic acid 2-ethyl ester obtained by a method similar to that in Synthetic Example 33 was subjected to acylation with decanoyl chloride in the presence of triethylamine to give N-decanoylthiazolidine-2,4-dicarboxylic acid 2-ethyl ester (with the ratio of two kinds of stereoisomers of about 46:54 as confirmed by NMR) as white crystals (61.2%).

$^1$H-NMR (CDCl$_3$, 400 MHz): δ; isomer A: 0.88 (3H, t, 7.14 Hz), 1.26-1.34 (12H, m), 1.29 (3H, t, J=7.18 Hz), 1.66-1.61 (2H, m), 2.28-2.36 (2H, m), 3.42 (1H, d, J=12.0 Hz), 3.68 (1H, dd, J=6.52, 12.0 Hz), 4.21 (2H, q, J=7.11 Hz), 4.96 (1H, d, J=6.23 Hz), 5.36 (1H, s). isomer B: 0.88 (3H, t, 7.14 Hz), 1.26-1.34 (12H, m), 1.32 (3H, t, J=7.19 Hz), 1.61-1.66 (2H, m), 2.09-2.17 (1H, m), 2.28-2.36 (1H, m), 3.36 (1H, d, J=12.2 Hz), 3.54 (1H, dd, J=7.13, 12.2 Hz), 4.25-4.31 (2H, m), 5.18 (1H, d, J=6.84 Hz), 5.25 (1H, s).

Synthetic Example 35

N-decanoylthiazolidine-2,4-dicarboxylic acid

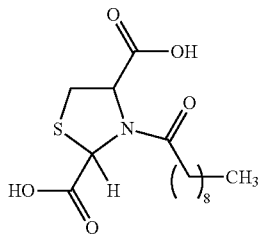

N-Decanoylthiazolidine-2,4-dicarboxylic acid 2-ethyl ester obtained by a method similar to that in Synthetic Example 34 was subjected to hydrolysis with sodium hydroxide (water-ethanol solvent) to give N-decanoylthiazolidine-2,4-dicarboxylic acid (with the ratio of two kinds of stereoisomers of about 24:76 as confirmed by NMR) as a white solid (79.1%).

$^1$H-NMR (CDCl$_3$, 400 MHz): δ; isomer A: 0.86 (3H, t, 6.84 Hz), 1.20-1.32 (12H, m), 1.45-1.55 (2H, m), 1.95-2.00 (1H, m), 2.11-2.19 (1H, m), 3.22 (1H, d, J=11.8 Hz), 3.47 (1H, dd, J=5.91, 11.8 Hz), 4.84 (1H, d, J=6.96 Hz), 5.55 (1H, s). isomer B: 0.86 (3H, t, 6.84 Hz), 1.20-1.32 (12H, m), 1.45-1.55 (2H, m), 5.23 (1H, dd, J=0.920, 5.82 Hz), 2.11-2.19 (1H, m), 2.35-2.44 (1H, m), 3.39-3.45 (2H, m), 5.06 (1H, s).

Synthetic Example 36

N-decanoylthiazolidine-2,4-dicarboxylic acid 2,4-diethyl ester

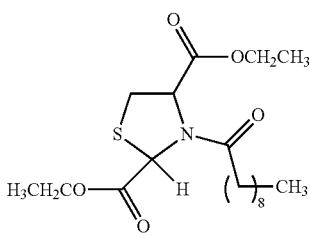

N-Decanoylthiazolidine-2,4-dicarboxylic acid 2-ethyl ester obtained by a method similar to that in Synthetic Example 34 was subjected to ethyl-esterification with ethanol, EDCI HCl, and DMAP to give N-decanoylthiazolidine-2,4-dicarboxylic acid 2,4-diethyl ester (the ratio of two kinds of stereoisomers was about 21:79) as a yellow wax substance (82.7%).

$^1$H-NMR (CDCl$_3$, 400 MHz): δ; isomer A: 0.87 (3H, t, 6.88 Hz), 1.25-1.33 (18H, m), 1.63-1.67 (2H, m), 2.24-2.30 (2H, m), 3.37 (1H, dd, J=0.640, 11.8 Hz), 3.66 (1H, dd, J=6.44, 11.8 Hz), 4.18-4.24 (4H, m), 4.90 (1H, d, J=5.96 Hz), 5.35 (1H, s). isomer B: 0.87 (3H, t, 6.88 Hz), 1.25-1.33 (18H, m), 1.63-1.67 (2H, m), 2.05-2.15 (1H, m), 2.26-2.30 (1H, m), 3.16 (1H, dd, J=0.780, 12.2 Hz), 3.58 (1H, dd, J=7.22, 12.2 Hz), 4.25-4.29 (4H, m), 5.15 (1H, d, J=6.60 Hz), 5.28 (1H, s).

Synthetic Example 37

N-acetylthiazolidine-2,4-dicarboxylic acid 2,4-dimethyl ester

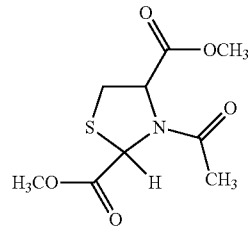 [SMILES: COC(=O)C1CSC(C(=O)OC)N1C(C)=O]

Thiazolidine-2,4-dicarboxylic acid (1.00 g, 5.67 mmol) synthesized from L-cysteine and glyoxylic acid (aqueous solution) were added to a methanol solution (15 ml) of thionyl chloride (22.6 mmol), and the mixture was stirred at room temperature for 16 hours. The reaction mixture was concentrated, and to the residue was added ether. The crystals were collected by filtration, washed with ether, and dried under reduced pressure to give thiazolidine-2,4-dicarboxylic acid 2,4-dimethyl ester hydrochloride as crystals (1.29 g, 94.0%).

Thiazolidine-2,4-dicarboxylic acid 2,4-dimethyl ester hydrochloride (0.50 g, 2.07 mmol) was subjected to acylation with acetyl chloride (0.22 ml, 3.09 mmol) in the presence of triethylamine (0.58 ml, 4.17 mmol) to give N-acetylthiazolidine-2,4-dicarboxylic acid 2,4-dimethyl ester (with the ratio of two kinds of stereoisomers of about 49:51 as confirmed by NMR) as a pale-yellow oil (0.42 g, 83.0%).

$^1$H-NMR (CDCl$_3$, 400 MHz): δ; isomer A: 2.17 (3H, s), 3.43 (1H, dd, J=7.02, 11.5 Hz), 3.69 (1H, dd, J=4.62, 11.5 Hz), 3.75 (3H, s), 3.85 (3H, s), 4.85 (1H, dd, J=4.64, 7.00 Hz), 5.77 (1H, s). isomer B: 5.36 (1H, s), 2.21 (3H, s), 3.34 (1H, dd, J=7.18, 11.5 Hz), 3.52 (1H, dd, J=7.92, 11.5 Hz), 3.78 (3H, s), 3.82 (3H, s), 5.05 (1H, t, J=7.56 Hz).

Synthetic Example 38

N-acetyl-2-[3-hydroxy-5-(hydroxymethyl)-2-methyl-pyridin-4-yl]thiazolidine-4-carboxylic acid

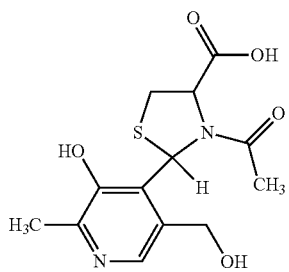 [SMILES: CC(=O)N1C(C(=O)O)CSC1c1c(CO)cnc(C)c1O]

L-Cysteine hydrochloride (8.00 g, 45.6 mmol), pyridoxal hydrochloride (8.80 g, 43.25 mmol), and sodium hydrogen carbonate (7.60 g, 90.5 mmol) were added to a mixed solvent of water (60 ml) and ethanol (120 ml), and the mixture was at stored −20° C. for 2 days. The precipitated solid was collected by filtration, and dried under reduced pressure to give 2-[3-hydroxy-5-(hydroxymethyl)-2-methylpyridin-4-yl]thiazolidine-4-carboxylic acid as a pale-yellow solid (10.73 g).

To water (1.06 ml) were added 2-[3-hydroxy-5-(hydroxymethyl)-2-methylpyridin-4-yl]thiazolidine-4-carboxylic acid (500 mg, 1.85 mmol) and acetic anhydride (1.06 ml, 11.1 mmol), and the mixture was heated at 80° C. for 1 hour. The reaction mixture was concentrated under reduced pressure, to the residue was added toluene (5 ml×3), and the mixture was concentrated under reduced pressure to give N-acetyl-2-[3-hydroxy-5-(hydroxymethyl)-2-methylpyridin-4-yl]thiazolidine-4-carboxylic acid as an amorphous solid (0.64 g).

To the above-mentioned solid (75 mg) was added ether, and the mixture was stirred for a while. The precipitate was collected by filtration, and dried under reduced pressure to give N-acetyl-2-[3-hydroxy-5-(hydroxymethyl)-2-methyl-pyridin-4-yl]thiazolidine-4-carboxylic acid (with the ratio of two kinds of stereoisomers of about 19:81 as confirmed by NMR)(53 mg) as a powder.

$^1$H-NMR (CDCl$_3$, 400 MHz): δ; isomer A: 2.29 (3H, s), 3.24 (1H, dd, J=2.49, 10.6 Hz), 3.39 (1H, dd, J=4.52, 10.7 Hz), 4.43 (2H, dd, J=12.74, 15.4 Hz), 4.49 (1H, dd, J=2.20, 6.51 Hz), 6.05 (1H, s), 7.78 (1H, s). isomer B: 2.32 (3H, s), 3.15 (1H, dd, J=8.38, 10.4 Hz), 3.36 (1H, dd, J=6.82, 10.4 Hz), 4.02 (1H, t, J=5.57 Hz), 4.46 (2H, dd, J=6.80, 13.1 Hz), 5.88 (1H, s), 7.81 (1H, s).

Synthetic Example 39

N-acetyl-2-(1,2,3,4,5-pentahydroxypentyl)thiazolidine-4-carboxylic acid methyl ester

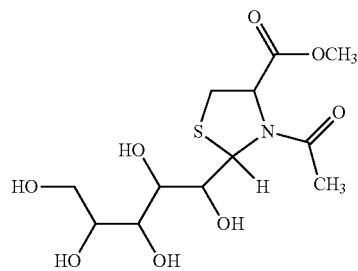 [SMILES: COC(=O)C1CSC(C(O)C(O)C(O)C(O)CO)N1C(C)=O]

Under an argon atmosphere, L-cysteine (2.42 g, 20.0 mmol), D-galactose (3.60 g, 20.0 mmol), and pyridine (0.40 ml, 5.0 mmol) were added to water (340 ml), and the solution was heated at 65° C. for 1 hour, and left standing at room temperature for 2 hours. The precipitated solid was collected by filtration, and dried under reduced pressure to give 2-(1,2,3,4,5-pentahydroxypentyl)thiazolidine-4-carboxylic acid (4.70 g) as white crystals.

Under an argon atmosphere, pyridine (28 ml, 346 mmol) was kept at 0° C., acetic anhydride (20 ml, 212 mmol) and 2-(1,2,3,4,5-pentahydroxypentyl)thiazolidine-4-carboxylic acid (2.0 g, 7.06 mmol) were added thereto, and the mixture was stirred at room temperature for 2 hours. The reaction mixture was concentrated under reduced pressure, to the residue was added ethanol (20 ml), and the mixture was stirred. The precipitated solid was collected by filtration, and dried under reduced pressure to give 8-acetyl-4-[1,2,3,4-tetrakis(acetoxy)butyl]-3-oxa-6-thia-8-azabicyclo[3.2.1]octan-2-one as white crystals (2.49 g).

The obtained white crystals (1.0 g, 2.10 mmol) were dissolved in methanol, and triethylamine (2.1 ml, 15.12 mmol) was added thereto. The reaction mixture was stirred at room temperature for 16 hours, and concentrated under reduced pressure. To the residue were added methanol and water, the mixture was stirred, and the precipitate was collected by filtration, and dried under reduced pressure to give N-acetyl-2-(1,2,3,4,5-pentahydroxypentyl)thiazolidine-4-carboxylic acid methyl ester as white crystals (627 mg).

$^1$H-NMR (D$_2$O, 400 MHz) δ; 2.23 (3H, s), 3.24 (1H, dd, J=9.16, 11.72 Hz), 3.43 (1H, dd, J=8.36, 12.36 Hz), 3.61-3.65 (3H, m), 3.72 (3H, s), 3.84-3.95 (3H, m), 4.91 (1H, t, J=8.68 Hz), 5.28 (1H, d, J=10.2 Hz). ESI-MS [M+H]$^+$=340.1, [M+Na]$^+$=362.0.

Synthetic Example 40

N-acetyl-2-(1,2,3,4,5-pentahydroxypentyl)thiazolidine-4-carboxylic acid

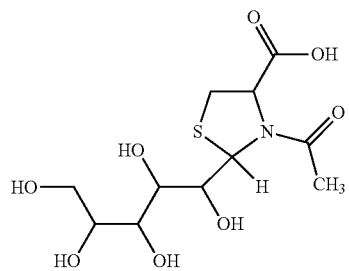 [SMILES: CC(=O)N1C(C(=O)O)CSC1C(O)C(O)C(O)C(O)CO]

8-Acetyl-4-[1,2,3,4-tetrakis(acetoxy)butyl]-3-oxa-6-this-8-azabicyclo[3.2.1]octan-2-one (202 mg, 0.42 mmol) obtained as an intermediate in Synthetic Example 39 was dissolved in a mixed solvent of methanol (1.5 ml) and water (1 ml), and 2N NaOH (0.84 ml) was added thereto. The reaction mixture was stirred for 16 hours, and the pH of the reaction mixture was adjusted to 3 with amberlite IR120B H AG. The amberlite IR120B H AG was removed by filtration, and the filtrate was concentrated under reduced pressure. A small amount of methanol was added thereto, and then ether was added thereto. The precipitated crystals were collected by filtration, and dried under reduced pressure to give N-acetyl-2-(1,2,3,4,5-pentahydroxypentyl)thiazolidine-4-carboxylic acid as white crystals (70 mg).

$^1$H-NMR (D$_2$O, 400 MHz) δ: 2.22 (3H, s), 3.25 (1H, t, J=4.72 Hz), 3.39-3.51 (1H, m), 3.57-3.64 (3H, m), 3.80-3.91 (3H, m), 4.84 (1H, t, J=8.80 Hz), 5.28 (1H, d, J=10.1 Hz). ESI-MS [M+Na]$^+$=348.0, [M−H]$^-$=323.9.

Synthetic Example 41

N-acetyl-2-methylthiazolidine-2,4-dicarboxylic acid 2-ethyl ester

L-2-Methylthiazolidine-2,4-dicarboxylic acid 2-ethyl ester (2.00 g, 9.13 mmol) obtained by a method similar to that in Reference Example 2 was dissolved in dichloromethane (19 ml), and the solution was kept at 0° C. To the reaction mixture was added potassium carbonate (2.54 g, 18.4 mmol), and acetyl chloride (0.97 ml, 13.7 mmol) was added dropwise thereto. The reaction temperature was allowed to gradually rise, and the mixture was stirred at room temperature for 16 hours. To the reaction mixture was added 5% aqueous citric acid (30 ml), and the mixture was extracted with dichloromethane (20 ml×2). The dichloromethane layer was washed with water (10 ml×2) and saturated brine (10 ml×2), and dried over anhydrous magnesium sulfate. The magnesium sulfate was removed by filtration, and the filtrate was concentrated under reduced pressure to give a colorless oil. To the oil was added a small amount of n-hexane. The oil became solidified. The crystals were collected by filtration, washed with n-hexane, and dried under reduced pressure to give N-acetyl-2-methylthiazolidine-2,4-dicarboxylic acid 2-ethyl ester (with the ratio of cis form:trans form of 96:4 as confirmed by HPLC) as colorless crystals (0.847 g). The melting point of the obtained crystal was measured using digital melting point measuring apparatus IA9100 manufactured by Electrothermal to be 101° C. to 105° C.

$^1$H-NMR (CDCl$_3$, 400 MHz): δ: cis: 1.39 (3H, t, J=7.13 Hz), 1.95 (3H, s), 2.16 (3H, s), 3.47 (1H, dd, J=1.66, 12.2 Hz), 3.72 (1H, dd, J=6.79, 12.2 Hz), 4.33-4.48 (2H, m), 4.98 (1H, dd, J=1.68, 6.78 Hz).

Comparison Synthetic Example 1

Synthesis of N-acetyl-2-methylthiazolidine-2,4-dicarboxylic acid according to the method described in J. Biological Chem., (1937) 121 539-48

Acetic anhydride (4.5 ml, 47.1 mmol) was kept at 0° C., 2-methylthiazolidine-2,4-dicarboxylic acid (3.0 g, 15.7 mmol) obtained by a method similar to that in Reference Example 1 and pyridine (3.8 ml, 47.1 mmol) were added thereto, and the reaction mixture was stirred at room temperature for 4 hours. To the reaction mixture was added 2N HCl (25 ml), and the mixture was extracted with ethyl acetate (100 ml). The ethyl acetate layer was washed with saturated brine (20 ml), and dried over anhydrous magnesium sulfate. The magnesium sulfate was removed by filtration, and the filtrate was concentrated under reduced pressure. A mixture of cis form and trans form of N-acetyl-2-methylthiazolidine-2,4-dicarboxylic acid and N-acetyl-2-methylthiazolidine-2,4-dicarboxylic acid anhydride was confirmed by measurement of the residue by $^1$H-NMR.

Experimental Example 1

Time-course Stability Test at 70° C.

Figure 2:
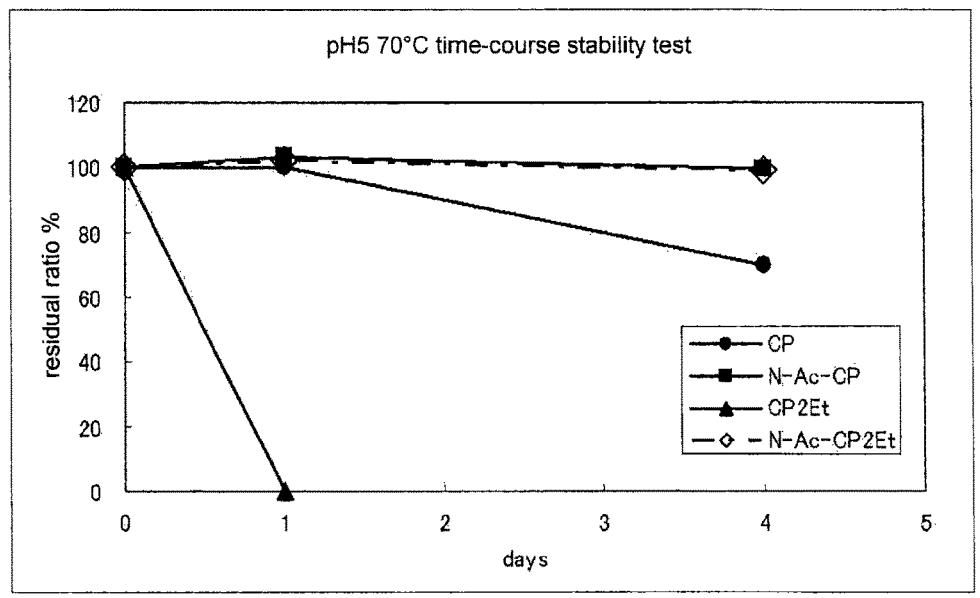
FIG. 2 shows the results of a time-course stability test of CP, N-Ac-CP, CP2Et and N-Ac-CP2Et at pH 5, 70° C.
Figure 3:
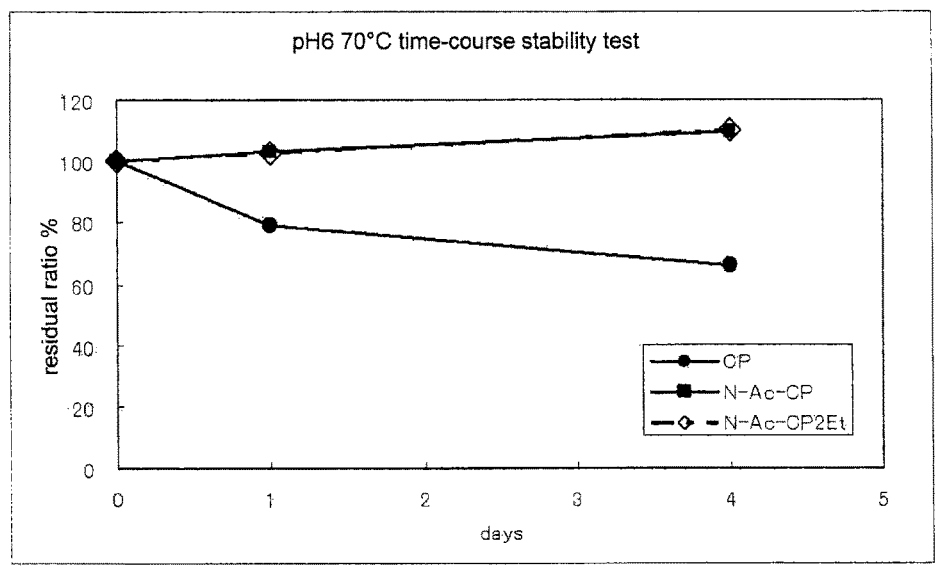
FIG. 3 shows the results of a time-course stability test of CP, N-Ac-CP and N-Ac-CP2Et at pH 6, 70° C.
Figure 4:
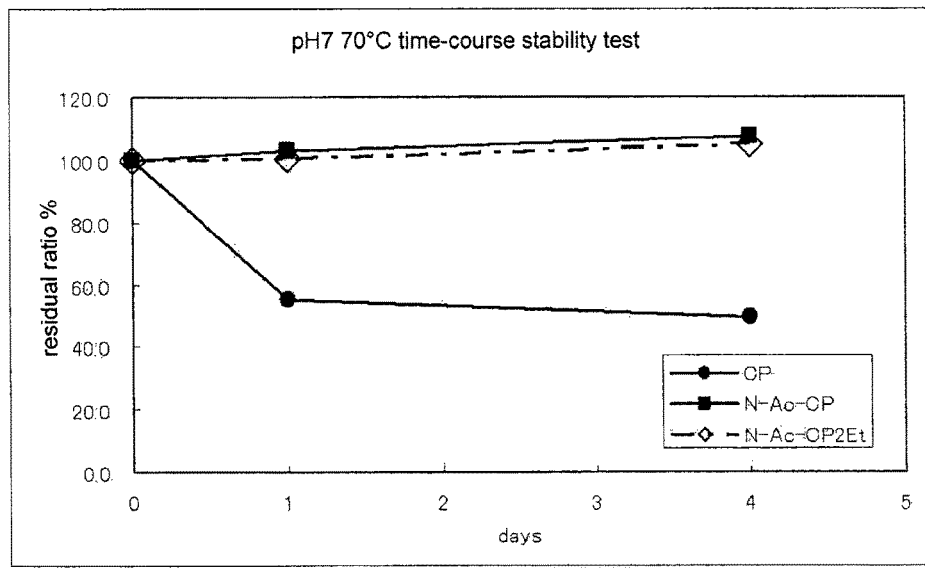
FIG. 4 shows the results of a time-course stability test of CP, N-Ac-CP and N-Ac-CP2Et at pH 7, 70° C.

A time-course stability test was performed using N-Ac-CP2Et obtained in Synthetic Example 1 and N-Ac-CP obtained in Synthetic Example 13 in a 25 mM phosphate buffer at pH 4, 5, 6, and 7 and 70° C. The test was performed for 4 days. The results are shown in FIGS. 1 to 4. As comparison targets, CP obtained in Reference Example 1, and CP2Et obtained in Reference Example 2 were used. For the time-course stability test, HPLC; (pump) HITACHI L-7100, (Autosampler) HITACHI L-2200, and (detector) HITACHI L-4000 were used.

As an index of a time-course stability test at 70° C., the area value of a target substance after time course changes relative to the area value of the target substance on day 0 after start of the stability test was calculated in % on an HPLC chart and used as a residual ratio.

HPLC Analysis Conditions
Conditions-1
detector: ultraviolet absorption spectrophotometer (measurement wavelength; 210 nm)
column: Inertsil ODS (GL Sciences) (particle size 3 μm, inner diameter 4.6 mm, length 250 mm)
eluent: 4 mL/L aqueous phosphoric acid solution:methanol=3:1 (v/v)
flow rate: 0.8 mL/minute
column temperature: 50° C.
sample concentration: 100 mg/dL
injection volume: 20 μL
retention time (minute): CP: 4.6, 4.8 (diastereomer mixture), N-Ac-CP: 8.0
Conditions-2
detector: ultraviolet absorption spectrophotometer (measurement wavelength; 210 nm)
column: Inertsil ODS-3 (High Pressure type, GL Sciences) (particle size 3 μm, inner diameter 4.6 mm, length 250 mm)

eluent: A: 0.05M $KH_2PO_4$ (adjusted to pH2 with 85% $H_3PO_4$), B: MeOH
gradient conditions: 0 to 5 minute: A=100, −25 minute: A:B=50:50, −35 minute: A:B=50:50, −40 minute: A=100, −45 min: A=100
flow rate: 0.8 mL/minute
column temperature: 30° C.
sample concentration: 25-50 mg/dL
injection volume: 20 μL
retention time (minute): N-Ac-CP: 21.7, CP2Et: 29.6, 29.8 (diastereomer mixture), N-Ac-CP2Et: 31.2

From FIGS. 1 to 4, it has been found that the cysteine derivative of the present invention (N-Ac-CP2Et, N-Ac-CP) shows preservation stability better than CP and CP2Et, and is a highly useful compound that reaches the practicalization level for cosmetics and the like.

Experimental Example 2

Time-course Stability Test at 70° C.

A time-course stability test was performed using about 1:1 mixture (20 mg/20 ml) of cis form-trans form of N-Ac-CP2Et obtained in Synthetic Example 7 in a 25 mM phosphate buffer at pH 4, 5, 6, and 7 and 70° C. in the same manner as in Examples Experimental Example 1. The test was performed for 5 days. As an index of a time-course stability test at 70° C., the area value of a target substance 5 days after start of the stability test relative to the area value of the target substance on day 0 after start of the stability test was calculated in % on an HPLC chart and used as a residual ratio. The results are shown in Table 1.
Detector: ultraviolet absorption spectrophotometer (measurement wavelength; 210 nm)
Column: Inertsil ODS-3 (High Pressure type, GL Sciences) (particle size 3 μm, inner diameter 4.6 mm, length 250 mm)
eluent: A: 0.05M $KH_2PO_4$ (adjusted to pH2 with 85% $H_3PO_4$), B: MeOH
gradient conditions: 0-5 minute: A=100, −25 minute: A:B=50:50, −35 minute: A:B=50:50, −40 minute: A=100, −45 minute: A=100
flow rate: 0.8 mL/minute
column temperature: 30° C.
sample concentration: 25-50 mg/dL
injection volume: 20 μL
retention time (minute): N-Ac-CP2Et (cis form): 31.9, N-Ac-CP2Et (trans form): 33.9

TABLE 1

|  | N-Ac-CP2Et (cis form) of Synthetic Example 7 | N-Ac-CP2Et (trans form) of Synthetic Example 7 |
| --- | --- | --- |
| residual ratio (%) at pH 4 | 69.9 | 95.8 |
| residual ratio (%) at pH 5 | 93.5 | 99.8 |
| residual ratio (%) at pH 6 | 96.9 | >99.9 |
| residual ratio (%) at pH 7 | >99.9 | >99.9 |

From Table 1, it has been found that both cis form and trans form of N-Ac-CP2Et, which is the cysteine derivative of the present invention, show good preservation stability. By comparison of the cis form and trans form, it has been found that the trans form is more superior in the stability under particularly acidic conditions (particularly, pH 5 or below).

Experimental Example 3

Odor Test 1 wt % Aqueous solutions (pH 4 or 7) of the cysteine derivatives of Synthetic Examples 10, 33, and 37, CP obtained in Reference Example 1, and CP2Et obtained in Reference Example 2 were prepared, tightly sealed, and preserved in a thermostatic tank at 70° C. for 4 days or 6 days. Each sample was taken out from the thermostatic tank, immediately thereafter smelled for odor by 6 panelists, and evaluated by the following criteria.
3 points: no sulfur odor was detected at all
2 points: slight sulfur odor was detected
1 point: sulfur odor was detected
0 point: strong sulfur odor was detected The results of the 6 panelists were totaled, and the total points were evaluated as ⊚: not less than 15 points, ◯: not less than 10 points and less than 15 points, Δ: not less than 5 points and less than 10 points, x: not less than 0 point and less than 5 points. The results are shown in Table 2.

TABLE 2

|  | cysteine derivative of Synthetic Example 10 | cysteine derivative of Synthetic Example 33 | cysteine derivative of Synthetic Example 37 | CP2Et | CP |
| --- | --- | --- | --- | --- | --- |
| evaluation at pH 4 (day 4) | ◯ (10 points) | ⊚ (16 points) | ◯ (10 points) | X (3 points) | X (6 points) |
| evaluation at pH 4 (day 6) | Δ (8 points) | ⊚ (15 points) | Δ (9 points) | X (1 points) | Δ (7 points) |
| evaluation at pH 7 (day 4) | ⊚ (18 points) | ⊚ (18 points) | ◯ (12 points) | X (3 points) | — (*) |
| evaluation at pH 7 (day 6) | ⊚ (17 points) | ⊚ (17 points) | Δ (9 points) | X (1 point) | — (*) |

* Since precipitate considered to be cysteine was confirmed, odor evaluation was not performed.

It has been found that the cysteine derivative of the present invention shows less odor and less sulfur odor due to decomposition and good preservation stability, and therefore, is a highly useful compound that reaches the practicalization level for cosmetics and the like.

Experimental Example 4

Eumelanin Production Suppression Test

B16 melanoma was cultured in DMEM (Dulbecco's Modified Eagle Medium) (high glucose, containing 10% serum). Confluent cells were detached with trypsin, and plated on a 96 well plate. After cell adhesion to the plate the next day, the medium was changed to DMEM added with each evaluation sample (control (no sample addition), cysteine derivatives of each Synthetic Example) at a predetermined evaluation concentration (diluted from 10 mM according to sample), and the cells were cultured for 3 days. The 96 well plate was shaken for 5 minutes in a plateshaker, and the absorbance of the medium at 450 nm was measured by a microplatereader. The absorbance after 3 days from the addition of a predetermined concentration of each sample was shown in relative percentage to the measured value (absorbance) of the control (no sample addition) as 100%, and the concentration necessary for suppressing eumelanin production in each sample by 50% was calculated as 50% melanin production suppressing concentration relative to the amount of eumelanin in the control as 100%. The results are shown in Table 3.

The microplatereader used in this eumelanin production suppression test was Benchmark microplatereader, manufactured by BIORAD.

TABLE 3

|  | 50% melanin production suppressing concentration |
|---|---|
| cysteine derivative of Synthetic Example 1 | 4538 μM |
| cysteine derivative of Synthetic Example 13 | 5474 μM |
| cysteine derivative of Synthetic Example 19 | 2606 μM |
| cysteine derivative of Synthetic Example 20 | 1420 μM |

It was found that the cysteine derivative of the present invention has an effect of suppressing the amount of eumelanin released from the cells.

INDUSTRIAL APPLICABILITY

It has been determined that the cysteine derivative of the present invention is superior in stability, and has less odor and sufficient eumelanin production suppressive effect. As a result, a whitening agent, a fleck improving agent or therapeutic agent, and a winkle improving agent or therapeutic agent, which have better stability and less odor than conventional L-cysteine derivatives, can be provided, as well as a cosmetic agent or skin external preparation containing such agent, which is superior in long-term preservation stability.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A cysteine compound represented by formula (I):

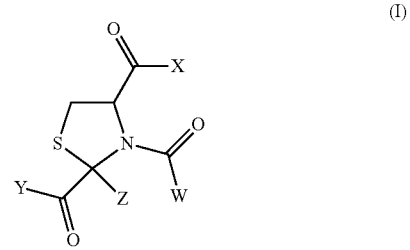

wherein
X and Y are each independently OR$^1$ or NHR$^2$ wherein R$^1$ and R$^2$ are each independently a hydrogen atom or a C$_{1-22}$ alkyl group or X and Y together are —O—;
Z is a hydrogen or C$_{1-22}$ alkyl group;
provided that when Z is a hydrogen atom, at least one of (i) and (ii) is satisfied;
(i) X is not methoxy, or
(ii) Y is not hydroxy; and
W is a C$_{1-22}$ alkyl group, a C$_{1-22}$ alkoxy group or a C$_{1-22}$ alkylamino group,
or a salt thereof;
and provided that said compound or a salt thereof is not:
N-acetyl-2-methylthiazolidine-2,4-dicarboxylic acid or a salt thereof,
N-acetyl-2-methylthiazolidine-2,4-dicarboxylic acid anhydride or a salt thereof, or
N-acetyl-2-methylthiazolidine-2,4-dicarboxylic acid 2-ethyl ester or a salt thereof.

2. A cysteine compound or salt thereof according to claim 1, which is in the trans form.

3. The cysteine compound or salt thereof according to claim 1, wherein Z is a C$_{1-22}$ alkyl group.

4. The cysteine compound or salt thereof according to claim 1, wherein Z is a hydrogen atom.

5. The cysteine compound or salt thereof according to claim 4, wherein X is not methoxy.

6. The cysteine compound or salt thereof according to claim 4, wherein Y is not hydroxy.

7. The cysteine compound or salt thereof according to claim 4, wherein X is not methoxy and Y is not hydroxy.

8. A method of producing a cysteine compound according to claim 1,
said method comprising:
reacting a compound represented by formula (IV):

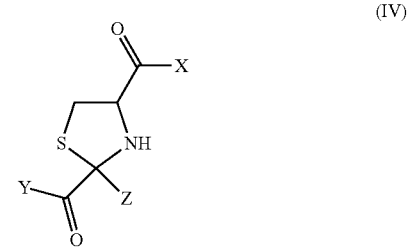

wherein each symbol is as defined in claim 1, with:
(a) a compound represented by formula (V):

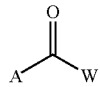

wherein
A is a halogen atom; and
W is as defined in claim 1, or
(b) a compound represented by formula (V'):

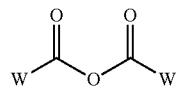

wherein W is as defined in claim 1.

9. A method of selectively producing a trans form of a cysteine compound according to claim 1, represented by formula (I'):

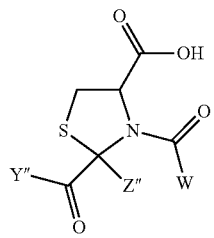

wherein
Y" is a $C_{1-22}$ alkoxy group;
Z" is a $C_{1-22}$ alkyl group; and
W is a $C_{1-22}$ alkyl group, a $C_{1-22}$ alkoxy group or a $C_{1-22}$ alkylamino group,
or a salt thereof, said method comprising:
reacting a compound represented by formula (IV'):

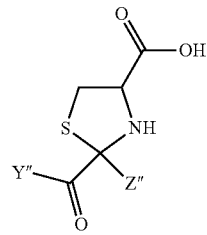

wherein each symbol is as defined above,
with:
(a) a compound represented by formula (V):

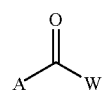

wherein
A is a halogen atom; and
W is as defined above,
in the presence of an organic base, or
(b) a compound represented by formula (V'):

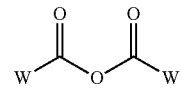

wherein W is as defined above,
in the absence of a base.

* * * * *